United States Patent
Samain et al.

(10) Patent No.: US 11,395,794 B2
(45) Date of Patent: *Jul. 26, 2022

(54) PROCESS FOR TREATING KERATIN FIBRES USING AN AQUEOUS COMPOSITION COMPRISING A COMBINATION OF PARTICULAR ALKOXYSILANES

(71) Applicant: L'OREAL, Paris (FR)

(72) Inventors: Henri Samain, Bièvres (FR); Nicolas Daubresse, La Celle Saint-Cloud (FR); Julien Cabourg, Combs la Ville (FR)

(73) Assignee: L'OREAL, Paris (FR)

( * ) Notice: Subject to any disclaimer, the term of this patent is extended or adjusted under 35 U.S.C. 154(b) by 387 days.

This patent is subject to a terminal disclaimer.

(21) Appl. No.: 16/061,796

(22) PCT Filed: Dec. 14, 2016

(86) PCT No.: PCT/EP2016/081024
§ 371 (c)(1),
(2) Date: Jun. 13, 2018

(87) PCT Pub. No.: WO2017/102856
PCT Pub. Date: Jun. 22, 2017

(65) Prior Publication Data
US 2018/0369107 A1 Dec. 27, 2018

(30) Foreign Application Priority Data
Dec. 14, 2015 (FR) ........................................ 1562328
Dec. 14, 2015 (FR) ........................................ 1562331

(51) Int. Cl.
*A61K 8/58* (2006.01)
*A61Q 5/06* (2006.01)
*A61Q 5/12* (2006.01)
*A61K 8/73* (2006.01)
*A61K 8/81* (2006.01)

(52) U.S. Cl.
CPC .............. *A61K 8/585* (2013.01); *A61K 8/731* (2013.01); *A61K 8/8147* (2013.01); *A61K 8/8158* (2013.01); *A61K 8/8182* (2013.01); *A61Q 5/06* (2013.01); *A61Q 5/12* (2013.01); *A61K 2800/48* (2013.01); *A61K 2800/49* (2013.01); *A61K 2800/95* (2013.01)

(58) Field of Classification Search
None
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,463,264 A | 3/1949 | Graenacher et al. |
| 2,723,248 A | 11/1955 | Wright |
| 2,798,053 A | 7/1957 | Brown |
| 2,923,692 A | 2/1960 | Ackerman et al. |
| 3,579,629 A | 5/1971 | Pasero et al. |
| 3,810,977 A | 5/1974 | Levine et al. |
| 3,915,921 A | 10/1975 | Schlatzer, Jr. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,128,631 A | 12/1978 | Lundmark et al. |
| 4,131,576 A | 12/1978 | Iovine et al. |
| 4,137,208 A | 1/1979 | Elliott |
| 4,237,243 A | 12/1980 | Quack et al. |
| 4,282,203 A | 8/1981 | Jacquet et al. |
| 4,289,752 A | 9/1981 | Mahieu et al. |
| 4,509,949 A | 4/1985 | Huang et al. |
| 4,585,597 A | 4/1986 | Lang et al. |
| 5,064,641 A | 11/1991 | Lang et al. |
| 5,089,578 A | 2/1992 | Valint et al. |
| 5,585,091 A | 12/1996 | Pelzer et al. |

(Continued)

FOREIGN PATENT DOCUMENTS

| | | |
|---|---|---|
| DE | 2330956 A1 | 1/1974 |
| EP | 0159628 A2 | 10/1985 |

(Continued)

OTHER PUBLICATIONS

International Search Report for Application No. PCT/EP/2016/081024, dated Feb. 8, 2017.
International Search Report for counterpart Application No. PCT/EP2016/081025, dated Feb. 8, 2017.
Fonnum, G., et al., "Associative Thickeners. Part I: Synthesis, Rheology and Aggregation Behavior," Colloid Polym. Sci., 271, (1993) pp. 380-389.
Morishima, Yotaro, "Self-Assembling Amphiphilic Polyelectrolytes and their Nanostructures," Chinese Journal of Polymer Science, vol. 18, No. 40, (2000), pp. 323-336.

(Continued)

*Primary Examiner* — Abigail Vanhorn
*Assistant Examiner* — Ali S Saeed
(74) *Attorney, Agent, or Firm* — The Marbury Law Group, PLLC

(57) ABSTRACT

The invention relates to a process for treating keratin fibres, which comprises the application of a composition comprising: (a) one or more alkoxysilanes comprising solubilizing function(s) of formula $R_1Si(OR_2)_z(R_3)_x(OH)_y$, and/or hydrolysis products thereof and/or oligomers thereof, (b) one or more alkylalkoxysilanes of formula $(R_4)_mSi(OR_5)_n$ and/or hydrolysis products thereof and/or oligomers thereof, and (c) water in an amount of greater than 30% by weight relative to the total weight of the composition. The invention also relates to a composition comprising components (a), (b) and (c), and (d) one or more thickeners.

12 Claims, No Drawings

(56) References Cited

U.S. PATENT DOCUMENTS

| | | | |
|---|---|---|---|
| 5,618,523 | A | 4/1997 | Zysman et al. |
| 5,773,611 | A | 6/1998 | Zysman et al. |
| 6,822,039 | B1 | 11/2004 | Monfreux-Gaillard et al. |
| 6,953,584 | B1 | 10/2005 | Samain et al. |
| 10,933,007 | B2 * | 3/2021 | Mathonneau ............ A61Q 5/02 |
| 2008/0226576 | A1 | 9/2008 | Benabdillah et al. |
| 2011/0200654 | A1 | 8/2011 | Habar |
| 2013/0255709 | A1 | 10/2013 | Khenniche et al. |
| 2015/0290093 | A1 * | 10/2015 | Salvemini ............... A61K 8/22 132/208 |

FOREIGN PATENT DOCUMENTS

| | | | | |
|---|---|---|---|---|
| EP | 0173109 | A2 | 3/1986 | |
| EP | 0503853 | A2 | 9/1992 | |
| EP | 0669323 | A1 | 8/1995 | |
| EP | 0750899 | A2 | 1/1997 | |
| EP | 1736139 | A1 | 12/2006 | |
| FR | 1222944 | A | 6/1960 | |
| FR | 1564110 | A | 4/1969 | |
| FR | 1580545 | A | 9/1969 | |
| FR | 2198719 | A1 | 4/1974 | |
| FR | 2265781 | A1 | 10/1975 | |
| FR | 2265782 | A1 | 10/1975 | |
| FR | 2350384 | A1 | 12/1977 | |
| FR | 2357241 | A2 | 2/1978 | |
| FR | 2416723 | A1 | 9/1979 | |
| FR | 2439798 | A1 | 5/1980 | |
| FR | 2528420 | A1 | 12/1983 | |
| FR | 2639347 | A1 | 5/1990 | |
| FR | 2673179 | A1 | 8/1992 | |
| FR | 2783164 | A1 | 3/2000 | |
| FR | 2910275 | A1 | 6/2008 | |
| FR | 2910276 | A1 | 6/2008 | |
| FR | 2937248 | A1 * | 4/2010 | ............ B01J 13/16 |
| FR | 2937248 | A1 | 4/2010 | |
| FR | 2964869 | A1 | 3/2012 | |
| FR | 2966355 | A1 | 4/2012 | |
| FR | 2966356 | A1 | 4/2012 | |
| FR | 3004932 | A1 | 10/2014 | |
| FR | 3004933 | A1 | 10/2014 | |
| FR | 3008888 | A1 | 1/2015 | |
| GB | 839805 | A | 6/1960 | |
| GB | 922457 | A | 4/1963 | |
| GB | 1408388 | A | 10/1975 | |
| GB | 1572626 | A | 7/1980 | |
| LU | 75370 | A1 | 2/1978 | |
| LU | 75371 | A1 | 2/1978 | |
| WO | 98/44012 | A1 | 10/1998 | |
| WO | 00/31154 | A1 | 6/2000 | |
| WO | 00/68282 | A1 | 11/2000 | |
| WO | 01/22931 | A1 | 4/2001 | |
| WO | 2012038880 | A2 | 3/2012 | |
| WO | WO-2012038880 | A2 * | 3/2012 | ............ A61Q 3/02 |
| WO | 2012055805 | A1 | 5/2012 | |
| WO | WO-2012055805 | A1 * | 5/2012 | ............ A61K 8/585 |
| WO | 2013083760 | A2 | 6/2013 | |
| WO | 2014/177628 | A1 | 11/2014 | |
| WO | 2015/011258 | A1 | 1/2015 | |
| WO | 2017/102857 | A1 | 6/2017 | |

OTHER PUBLICATIONS

Noda, Tetsuya, et al., "Micelle Formation of Random Copolymers of Sodium 2-(Acrylamido)-2-Methylpropanesulphonate and a Nonionic Surfactant Macromonomer in Water as Studied by Fluorescence and Dynamic Light Scattering," Macromolecules 2000, 33, pp. 3694-3704.

Noda, Tetsuya et al., "Solution Properties of Micelle Networks Formed by Nonionic Surfactant Moieties Covalently Bound to a Polyelectrolyte: Salt Effects on Rheological Behavior," Langmuir 2000, 16, pp. 5324-5332.

Noda, Tetsuya, et al., "Stimuli-Responsive Amphiphilic Copolymers of Sodium 2-(Acrylamido)-2-Methylpropanesulphonate and Associative Macromonomers," Polym. Preprint, Div. Polym. Chem. 1999, 40(2), pp. 220-221.

Todd, Charles, et al., "Volatile Silicone Fluids for Cosmetic Formulations," Cosmetics and Toiletries, vol. 91, Jan. 1976, pp. 29-32.

Wertz, et al., Essential Fatty Acids and Epidermal Integrity, Archive of Dermatology, vol. 123, Oct. 1987, pp. 1381-1384.

Anonymous: "Collacral Vai Technical Information," XP055340344, Apr. 1, 2015, p. 1. Retrieved from the Internet: https://www.dispersions-pigments.basf.com/portal/load/fid819942/TI_ED_1927_e_Collacral_VAL_187214_SCREEN_01.pdf [retrieved on Jan. 30, 2017].

Non-Final Office Action for co-pending U.S. Appl. No. 16/061,800, dated May 10, 2019.

* cited by examiner

PROCESS FOR TREATING KERATIN FIBRES USING AN AQUEOUS COMPOSITION COMPRISING A COMBINATION OF PARTICULAR ALKOXYSILANES

CROSS REFERENCE TO RELATED APPLICATIONS

This is a national stage application of PCT/EP2016/081024, filed internationally on Dec. 14, 2016, which claims priority to French Application Nos. 1562328 filed on Dec. 14, 2015, and U.S. Pat. No. 1,562,331 filed on Dec. 14, 2015, all of which are incorporated by reference herein in their entireties.

The present invention relates to a process for treating keratin fibres, in particular the hair, using a composition comprising a combination of particular alkoxysilanes, and at least 30% by weight of water relative to the total weight of the composition. The invention also relates to a composition comprising a combination of particular alkoxysilanes, at least 30% by weight of water relative to the total weight of the composition, and at least one thickener, and to the use thereof for the cosmetic treatment of keratin fibres, especially for shaping and/or conditioning the hair.

In the field of the cosmetic treatment of keratin fibres, especially human keratin fibres and better still the hair, the hair shaping is usually obtained by using polymer-based compositions, which makes it possible after drying to create a rigid, cohesive material, which in particular bonds the individual hairs together in the form of locks.

The ease of use and the quality of the hold obtained ensured the success of the lacquers, gels and mousses which extensively use such polymers.

However, polymers also have defects that have an influence on the technical qualities of the products: they may be tacky on use or during the removal process, give the hair a coarse feel, and create residues during brushing or simply when the hands are passed through the hair.

Moreover, the systems used for shaping generally have little resistance to mechanical stresses or to moisture. It is then necessary either to apply a large amount of product, thereby increasing the abovementioned problems, or to reapply the product and to restyle after a few hours.

Finally, it is not known how at the same time to provide a care treatment, all the less so a long-lasting care treatment and even less still long-lasting repair with these technologies.

To overcome the defects of polymers, other systems have been tested, and especially the technology of sol-gels, based mainly on alkoxysilane derivatives. Thus, the use of alkoxysilanes comprising an amino group, combined with acidic agents was described in patent application FR 2 783 164 for shaping and caring for the hair.

Uses of soluble alkoxysilane alone or in combination with a silicone or a cationic polymer are known from EP 1 216 022, FR 2 910 275 and FR 2 910 276, respectively, for styling and caring for the hair.

Particular alkyl-chain alkoxysilanes have also been described as agents for modifying the shape of the hair and as care agents, such as methyltriethoxysilane in WO 2007/032 314 and EP 1 736 139, or octyl triethoxysilane, in haircare compositions, optionally combined with a second silane such as aminopropyltriethoxysilane, for example in patent application FR 2 966 356.

The product of hydrolysis of methyltriethoxysilane is moreover referenced at the INCI under the name methylsilanetriol or silanetriol and is used in low concentration in many cosmetic preparations.

However, the use of these above systems has not hitherto made it possible to unite good working qualities on application, good hairstyling performance that is long-lasting, with care performance especially in terms of disentangling, in particular on wet hair, and softness or a uniform feel of the hair from the root to the end (smoothness), in particular on dried hair.

Furthermore, at and above a concentration of about 1% by weight in aqueous medium, substantial instability problems arise for compositions based on the majority of alkoxysilanes, in particular for methyltriethoxysilane: the aqueous solutions of this silane, and more generally of silanetriol, in fact rapidly show precipitates. In addition, a low concentration of alkoxysilane does not make it possible to obtain satisfactory fixing performance.

To overcome this drawback in particular, EP 1 736 139 thus proposes to prepare cosmetic compositions just before use, via a first step of hydrolysis of the alkoxy functions to silanol, these groups then being able to condense to form insoluble materials, which is impractical for the user and may lead to a lack of reproducibility of the effects.

It is thus particularly advantageous to obtain stable alkoxysilane-based systems, which are sufficiently concentrated to be effective both for shaping and for caring for the hair. Stable compositions comprising alkoxysilanes are described in French patent applications 3 004 932 and 3 004 933, but they comprise low concentrations of water, namely less than 30% by weight relative to the total weight of the composition. In addition, they are used as nail varnishes, and when they are applied to hair, they have a tacky nature.

There is thus a need to develop hairstyling and haircare compositions which make it possible to overcome the drawbacks mentioned above.

The Applicant has now discovered that the combined use of at least two particular different alkoxysilanes in a composition containing at least 30% by weight of water, and optionally at least one thickener, makes it possible to obtain a composition which is stable over time, and which aids in styling the hair, for example during hairsetting, the formation of locks, or blow-drying, with good resistance to mechanical stresses or to exposure to moisture, while at the same time having conditioning power, especially in terms of softness and a smooth feel, which is perceptible during application, once the product has dried and the hair has been shaped. This care effect is also perceptible after removal of the product by brushing, or else during ensuing treatments applied to the hair, and most particularly during subsequent shampooing.

Moreover, the compositions according to the invention are homogeneous, i.e. they do not have any precipitates.

They may be in single-phase or multi-phase form, for instance two-phase systems (visually distinct liquid phases), or emulsions.

For the purposes of the present invention, the term "stable over time" means that the visual appearance and the viscosity of the compositions do not change or do not substantially change (variation generally less than 10% relative to the viscosity at T0) over time under standard storage conditions, for example for one month or two months following the manufacture of said compositions, at 4° C., at room temperature (20-25° C.) and at 45° C. It also means that the performance obtained does not change or does not substantially change during the storage of the formulations.

The process using the composition makes it possible to have identical shaping and haircare results the day after manufacture of the composition and several months after its manufacture.

Unlike conventional systems, this composition makes it possible, after its application and shaping, to obtain hair that is not coarse, tacky or greasy. The hair is fixed and has a soft feel. Moreover, repeated application of the compositions leads to an increase in the level of haircare, a gain in mass and tonicity, where appropriate, for hair that is considered too fine, without adverse effects such as an overaccumulation of product and difficulty in the disentangling. The locks obtained may be stiff, but can be touched without losing shape or forming white films or residues on the hair. Removal of the majority of the product is obtained simply during a first shampoo wash, but an effect may also remain over time, of care type, especially in terms of wet or dry disentangling, manageability and smooth feel, which is still perceptible after a few shampoo washes.

Furthermore, said composition improves the durability of colouring effects with respect to shampooing.

One subject of the invention is thus a process for treating keratin fibres, preferably the hair, and more particularly for shaping and/or conditioning the hair, which comprises the application of a composition (A) comprising:

(a) one or more alkoxysilanes bearing solubilizing function(s) of formula (I) below, and/or hydrolysis products thereof and/or oligomers thereof:

$$R_1Si(OR_2)_z(R_3)_x(OH)_y \quad (I)$$

in which:
$R_1$ is a linear or branched, saturated or unsaturated, cyclic or acyclic $C_1$-$C_6$ hydrocarbon-based chain substituted with one or more groups chosen from the following groups:
  amine $NH_2$ or $NHR$, $R$ being:
    a $C_1$-$C_{20}$ and preferably $C_1$-$C_6$ alkyl group optionally substituted with a group comprising a silicon atom,
    a $C_3$-$C_{40}$ cycloalkyl group or
    a $C_6$-$C_{30}$ aromatic group,
  hydroxyl,
  thiol,
  aryl or aryloxy substituted with an amino group or with a $C_1$-$C_4$ aminoalkyl group,
$R_1$ possibly being interrupted with a heteroatom such as O, S or NH, or a carbonyl group (CO),
$R_2$ and $R_3$, which may be identical or different, represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with $z+x+y=3$,
(b) one or more alkylalkoxysilanes of formula (III) below, and/or hydrolysis products thereof and/or oligomers thereof:

$$(R_4)_m Si(OR_5)_n \quad (III)$$

in which:
$R_4$ and $R_5$ each represent, independently of each other, a $C_{1-6}$, better still $C_{1-4}$, alkyl group such as methyl, ethyl, n-propyl, isopropyl, n-butyl, isobutyl and tert-butyl, preferably methyl, ethyl and n-propyl,
n ranges from 1 to 3,
m ranges from 1 to 3,
on condition that $m+n=4$, and
(c) water in an amount of greater than 30% by weight relative to the total weight of the composition.

Other subjects, characteristics, aspects and advantages of the invention will emerge even more clearly on reading the description and the examples that follow.

In the text hereinbelow, unless otherwise indicated, the limits of a range of values are included in that range, in particular in the expressions "between" and "ranging from . . . to . . . ".

The expression "at least one" used in the present description is equivalent to the expression "one or more".

According to the invention, the process for treating keratin fibres, especially the hair, comprises the application of a composition (A) comprising:
(a) one or more alkoxysilanes bearing solubilizing function(s) of formula (I) as defined in the present application, and/or hydrolysis products thereof and/or oligomers thereof;
(b) one or more alkylalkoxysilanes of formula (III) as defined in the present application, and/or hydrolysis products thereof and/or oligomers thereof; and
(c) water in an amount of greater than 30% by weight relative to the total weight of the composition.

The term "oligomer" used in the invention means the polymerization products of the compounds to which the term "oligomer" relates, comprising from 2 to 10 silicon atoms.

In the present invention, the expression "alkoxysilane(s) bearing solubilizing function(s) (a)" covers the alkoxysilane(s) bearing solubilizing function(s) of formula (I) below, and/or hydrolysis product(s) thereof and/or oligomer(s) thereof:

$$R_1Si(OR_2)_z(R_3)_x(OH)_y \quad (I)$$

in which:
$R_1$ is a linear or branched, saturated or unsaturated, cyclic or acyclic $C_1$-$C_6$ hydrocarbon-based chain substituted with one or more groups chosen from the following groups:
  amine $NH_2$ or $NHR$, $R$ being:
    a $C_1$-$C_{20}$ and preferably $C_1$-$C_6$ alkyl group optionally substituted with a group comprising a silicon atom,
    a $C_3$-$C_{40}$ cycloalkyl group or
    a $C_6$-$C_{30}$ aromatic group,
  hydroxyl,
  thiol,
  aryl or aryloxy substituted with an amino group or with a $C_1$-$C_4$ aminoalkyl group,
$R_1$ possibly being interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with $z+x+y=3$.

More particularly, the alkoxysilanes comprising solubilizing function(s) (a) comprise at least one amino group in their structure.

Preferably, $R_1$ is an acyclic chain.

Preferably, $R_1$ is a linear or branched, saturated or unsaturated $C_1$-$C_6$ hydrocarbon-based chain, substituted with an amine group $NH_2$ or $NHR$, $R$ being:
  a $C_1$-$C_{20}$ and preferably $C_1$-$C_6$ alkyl group optionally substituted with a group comprising a silicon atom, better still a group $(R_2O)_3Si$—, a $C_3$-$C_{40}$ cycloalkyl or
a $C_6$-$C_{30}$ aromatic group.

Preferably, $R_2$ represents an alkyl group comprising from 1 to 4 carbon atoms, better still a linear alkyl group comprising from 1 to 4 carbon atoms, and is preferably the ethyl group.

Preferably, $R_3$ represents an alkyl group comprising from 1 to 4 carbon atoms, better still a linear alkyl group comprising from 1 to 4 carbon atoms, and preferably represents a methyl group or an ethyl group.

Preferably, the compound of formula (I) comprises only one or two silicon atoms in its structure.

Preferably, z ranges from 1 to 3. Even more preferentially, z is equal to 3 and thus x=y=0.

Preferably, the alkoxysilane(s) bearing solubilizing function(s) (a) according to the invention are chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxy-silane, p-aminophenyltrimethoxysilane, N-(2-aminoethylaminomethyl)phenethyl-trimethoxysilane and bis[3-(triethoxysilyl)propyl]amine, oligomers thereof, hydrolysis products thereof and a mixture of these compounds, better still from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and bis[3-(triethoxysilyl)propyl]amine, oligomers thereof, hydrolysis products thereof and a mixture of these compounds, and in particular the alkoxysilane(s) bearing solubilizing function(s) (a) are chosen from 3-aminopropyltriethoxysilane (APTES), hydrolysis products thereof, oligomers thereof and a mixture of these compounds.

According to one preferred embodiment, the alkoxysilane(s) comprising solubilizing function(s) (a) are chosen from the compounds of formula (II) below, and/or oligomers thereof and/or hydrolysis products thereof:

$$H_2N(CH_2)_n\text{—}Si(OR')_3 \quad (II)$$

in which the R' groups, which may be identical or different, are chosen from linear or branched $C_1$-$C_6$ alkyl groups and n" is an integer ranging from 1 to 6 and preferably from 2 to 4.

An alkoxysilane bearing solubilizing function(s) (a) that is particularly preferred according to this embodiment is 3-aminopropyltriethoxysilane (APTES) and/or hydrolysis products thereof and/or oligomers thereof.

Said alkoxysilane(s) bearing solubilizing function(s) (a) used in composition (A) according to the invention may represent from 0.5% to 50% by weight, preferably from 1% to 30% by weight, and in particular from 2% to 25% by weight, relative to the total weight of composition (A).

The second essential ingredient (b) of composition (A) is an alkylalkoxysilane of formula (III) below, and/or hydrolysis products thereof and/or oligomers thereof:

$$(R_4)_m Si(OR_5)_n \quad (III)$$

in which:
$R_4$ and $R_5$ each represent, independently of each other, a $C_{1-6}$, better still $C_{1-4}$, alkyl group such as methyl, ethyl, n-propyl, isopropyl, n-butyl, isobutyl and tert-butyl, preferably methyl, ethyl or n-propyl,
n ranges from 1 to 3,
m ranges from 1 to 3,
on condition that m+n=4.

Preferably, $R_5$ represents a methyl, ethyl or n-propyl group, n=3 and m=1.

Preferably, the oligomers of the compounds of formula (III) are water-soluble.

As examples of alkylalkoxysilanes (b) that are particularly preferred, mention may be made especially of methyltriethoxysilane (MTES), methyltripropoxysilane, oligomers thereof and/or hydrolysis products thereof.

In the present invention, the term "alkylalkoxysilane(s) (b)" encompasses the alkylalkoxysilane(s) of formula (III), and/or hydrolysis product(s) thereof and/or oligomer(s) thereof.

Said alkylalkoxysilanes (b) used in composition (A) according to the invention may represent from 0.1% to 50% by weight, preferably from 0.2% to 20% by weight, preferentially from 0.5% to 15% by weight, and in particular from 1% to 10% by weight, relative to the total weight of composition (A).

These two compounds (a) and (b) are preferably present in composition (A) according to the invention in an (a)/(b) weight ratio ranging from 0.5 to 10, more preferentially from 1 to 10, better still from 1.5 to 7.

Composition (A) according to the invention comprises as third essential ingredient at least 30% by weight, better still at least 50% by weight and even more preferentially at least 60% by weight of water, relative to the total weight of the composition.

More particularly, the amount of water ranges from 30% to 99% by weight, better still from 50% by weight or even 60% by weight to 99% by weight, even better still from 62% to 99% by weight and even more preferentially from 65% to 95% by weight, relative to the total weight of composition (A).

Composition (A) may also comprise one or more organic solvents that are liquid at 25° C. and 1.013×10$^5$ Pa and which are especially water-soluble, such as $C_1$-$C_7$ alcohols, especially $C_1$-$C_7$ aliphatic or aromatic monoalcohols, and $C_3$-$C_7$ polyols and polyol ethers, which may thus be used alone or as a mixture with water. Advantageously, the organic solvent may be chosen from ethanol and isopropanol, and mixtures thereof.

Composition (A) may also comprise one or more thickeners.

The term "thickener" means an agent which, when introduced at 1% by weight in an aqueous solution or an aqueous-alcoholic solution containing 30% ethanol, and at pH 7, or in an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of 1 s$^{-1}$. This viscosity may be measured using a cone/plate viscometer (Haake R600 rheometer or the like).

Preferably, the composition comprises one or more thickening polymers.

The thickening polymers according to the invention may be of natural or synthetic origin.

The thickening polymers may be associative or non-associative anionic, cationic, amphoteric or nonionic polymers.

It is recalled that "associative polymers" are polymers that are capable of reversibly associating with each other or with other molecules.

Their chemical structure more particularly comprises at least one hydrophilic region and at least one hydrophobic region.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a mono functional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Non-associative thickening polymers that may be mentioned include non-associative thickening polymers bearing sugar units.

For the purposes of the present invention, the term "sugar unit" means a unit derived from a carbohydrate of formula $C_n(H_2O)_{n-1}$ or $(CH_2O)_n$, which may be optionally modified by substitution and/or by oxidation and/or by dehydration.

The sugar units that may be included in the composition of the thickening polymers of the invention are preferably derived from the following sugars:
  glucose;
  galactose;
  arabinose;
  rhamnose;
  mannose;
  xylose;
  fucose;
  anhydrogalactose;
  galacturonic acid;
  glucuronic acid;
  mannuronic acid;
  galactose sulfate;
  anhydrogalactose sulfate and
  fructose.

Thickening polymers of the invention that may especially be mentioned include native gums such as:
  a) tree or shrub exudates, including:
  gum arabic (branched polymer of galactose, arabinose, rhamnose and glucuronic acid);
  ghatti gum (polymer derived from arabinose, galactose, mannose, xylose and glucuronic acid);
  karaya gum (polymer derived from galacturonic acid, galactose, rhamnose and glucuronic acid);
  gum tragacanth (or tragacanth) (polymer of galacturonic acid, galactose, fucose, xylose and arabinose);
  b) gums derived from algae, including:
  agar (polymer derived from galactose and anhydrogalactose);
  alginates (polymers of mannuronic acid and of glucuronic acid);
  carrageenans and furcellerans (polymers of galactose sulfate and of anhydrogalactose sulfate);
  c) gums derived from seeds or tubers, including:
  guar gum (polymer of mannose and galactose);
  locust bean gum (polymer of mannose and galactose);
  fenugreek gum (polymer of mannose and galactose);
  tamarind gum (polymer of galactose, xylose and glucose);
  konjac gum (polymer of glucose and mannose);
  d) microbial gums, including:
  xanthan gum (polymer of glucose, mannose acetate, mannose/pyruvic acid and glucuronic acid);
  gellan gum (polymer of partially acylated glucose, rhamnose and glucuronic acid);
  scleroglucan gum (glucose polymer);
  e) plant extracts, including:
  cellulose (glucose polymer);
  starch (glucose polymer) and
  inulin.

These polymers can be physically or chemically modified. As physical treatment, mention may especially be made of the temperature.

Chemical treatments that may be mentioned include esterification, etherification, amidation or oxidation reactions. These treatments make it possible to lead to polymers that may especially be nonionic, anionic or amphoteric.

Preferably, these chemical or physical treatments are applied to guar gums, locust bean gums, starches and celluloses.

The nonionic guar gums that may be used according to the invention may be modified with $C_1$-$C_6$ (poly)hydroxyalkyl groups.

Among the $C_1$-$C_6$ (poly)hydroxyalkyl groups, mention may be made, for example, of hydroxymethyl, hydroxyethyl, hydroxypropyl and hydroxybutyl groups.

These guar gums are well known in the prior art and may be prepared, for example, by reacting the corresponding alkene oxides, for instance, propylene oxides, with the guar gum so as to obtain a guar gum modified with hydroxypropyl groups.

The degree of hydroxyalkylation preferably varies from 0.4 to 1.2 and corresponds to the number of alkylene oxide molecules consumed by the number of free hydroxyl functional groups present on the guar gum.

Such nonionic guar gums optionally modified with hydroxyalkyl groups are sold, for example, under the trade names Jaguar HP8, Jaguar HP60, Jaguar HP105 and Jaguar HP120 by the company Rhodia Chimie.

The botanical origin of the starch molecules used in the present invention may be cereals or tubers. Thus, the starches are chosen, for example, from corn starch, rice starch, cassava starch, barley starch, potato starch, wheat starch, sorghum starch and pea starch.

The starches may be chemically or physically modified, especially by one or more of the following reactions: pregelatinization, oxidation, crosslinking, esterification, etherification, amidation, heat treatments.

Distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

According to the invention, amphoteric starches may also be used, these amphoteric starches comprising one or more anionic groups and one or more cationic groups. The anionic and cationic groups may be bonded to the same reactive site of the starch molecule or to different reactive sites; they are preferably bonded to the same reactive site. The anionic groups may be of carboxylic, phosphate or sulfate type, preferably carboxylic. The cationic groups may be of primary, secondary, tertiary or quaternary amine type.

The starch molecules may be derived from any plant source of starch, especially such as corn, potato, oat, rice, tapioca, sorghum, barley or wheat. It is also possible to use the hydrolysates of the starches mentioned above. The starch is preferably derived from potato.

The non-associative thickening polymers of the invention may be cellulose-based polymers not comprising a $C_{10}$-$C_{30}$ fatty chain in their structure.

According to the invention, the term "cellulose-based" polymer means any polysaccharide compound having in its structure sequences of glucose residues linked together via β-1,4 bonds; in addition to unsubstituted celluloses, the cellulose derivatives may be anionic, cationic, amphoteric or nonionic.

Thus, the cellulose-based polymers of the invention may be chosen from unsubstituted celluloses, including those in a microcrystalline form, and cellulose ethers.

Among these cellulose-based polymers, cellulose ethers, cellulose esters and cellulose ester ethers are distinguished.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers without a $C_{10}$-$C_{30}$ fatty chain, i.e. which are "non-associative", mention may be made of ($C_1$-$C_4$)alkylcelluloses, such as methylcelluloses and ethylcelluloses (for example, Ethocel standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$) alkyl-($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

Among the anionic cellulose ethers without a fatty chain, mention may be made of (poly)carboxy($C_1$-$C_4$)alkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers without a fatty chain, mention may be made of cationic cellulose derivatives such as cellulose copolymers or cellulose derivatives grafted with a water-soluble quaternary ammonium monomer, and described in particular in U.S. Pat. No. 4,131,576, such as (poly)hydroxy($C_1$-$C_4$)alkyl celluloses, for instance hydroxymethyl-, hydroxyethyl- or hydroxypropylcelluloses grafted especially with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

Among the non-associative thickening polymers not bearing sugar units that may be used, mention may be made of crosslinked acrylic or methacrylic acid homopolymers or copolymers, crosslinked 2-acrylamido-2-methylpropanesulfonic acid homopolymers and crosslinked acrylamide copolymers thereof, ammonium acrylate homopolymers, or copolymers of ammonium acrylate and of acrylamide, alone or mixtures thereof.

A first family of non-associative thickening polymers that is suitable for use is represented by optionally salified crosslinked acrylic acid homopolymers.

Among the homopolymers of this type, mention may be made of those crosslinked with an allyl alcohol ether of the sugar series, for instance, the products sold under the names Carbopol 980, 981, 954, 2984 and 5984 by the company Noveon or the products sold under the names Synthalen M and Synthalen K by the company 3 VSA.

The non-associative thickening polymers may also be crosslinked (meth)acrylic acid copolymers, such as the polymer sold under the name Aqua SF1 by the company Noveon.

The non-associative thickening polymers may be chosen from crosslinked 2-acrylamido-2-methylpropanesulfonic acid homopolymers and the crosslinked acrylamide copolymers thereof, and salts thereof.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as non-associative thickening polymers, ammonium acrylate homopolymers or copolymers of ammonium acrylate and of acrylamide.

Among the ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to documents FR 2 416 723, U.S. Pat. Nos. 2,798,053 and 2,923,692 as regards the description and preparation of such compounds.

Among the thickening polymers, mention may also be made of the associative polymers that are well known to a person skilled in the art and especially of nonionic, anionic, cationic or amphoteric nature.

Among the associative polymers of anionic type that may be mentioned are:
(a) those comprising at least one hydrophilic unit and at least one fatty-chain allyl ether unit, more particularly those whose hydrophilic unit is formed by an ethylenic unsaturated anionic monomer, more particularly a vinylcarboxylic acid and most particularly an acrylic acid or a methacrylic acid or mixtures thereof.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

The term "lower alkyl" used in the invention means a $C_1$-$C_6$, preferably $C_1$-$C_4$ alkyl group.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company BASF under the names Salcare SC 80® and Salcare SC 90®, which are aqueous 30% emulsions of a crosslinked terpolymer of methacrylic acid, of ethyl acrylate and of steareth-10 allyl ether (40/50/10).

(b) those comprising i) at least one hydrophilic unit of unsaturated olefinic carboxylic acid type, and ii) at least one hydrophobic unit of the type such as a ($C_{10}$-$C_{30}$) alkyl ester of an unsaturated carboxylic acid.

($C_{10}$-$C_{30}$) alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among anionic associative polymers of this type that will be used more particularly are those constituted of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those constituted of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP.

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(d) acrylic terpolymers comprising:
  i) about 20% to 70% by weight of an α,β-monoethylenically unsaturated carboxylic acid [Ac],
  ii) about 20% to 80% by weight of an α,β-monoethylenically unsaturated non-surfactant monomer other than [Ac],
  iii) about 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(e) copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® and Aculyn 88®, sold by the company Röhm & Haas, which are methacrylic acid/ethyl acrylate/oxyalkylenated stearyl methacrylate terpolymers, or else Aculyn 28®, sold by the company Röhm & Haas, which is a methacrylic acid/ethyl acrylate/oxyalkylenated behenyl methacrylate terpolymer.

Mention will also be made of the products sold by the company Lubrizol under commercial references CARBOPOL Ultrez 20 and CARBOPOL Ultrez 21, which are acrylic polymers (acrylates/C10-30 alkyl acrylate crosspolymer) and NOVETHIX L-10, which is an acrylates/beheneth-25 methacrylate copolymer.

(f) Associative polymers comprising at least one ethylenically unsaturated monomer bearing a sulfonic group, in free or partially or totally neutralized form and comprising at least one hydrophobic part. These polymers may be crosslinked or non-crosslinked. They are preferably crosslinked.

The ethylenically unsaturated monomers bearing a sulfonic group are especially chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will more particularly be used.

The polymers of this family may be chosen especially from random amphiphilic AMPS polymers modified by reaction with a $C_6$-$C_{22}$ n-monoalkylamine or di-n-alkylamine, and such as those described in patent application WO 00/31154 (which form an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or monoalkylene or polyalkylene glycols, (meth)acrylamides, vinylpyrrolidone, maleic anhydride, itaconic acid or maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, U.S. Pat. No. 5,089,578 and in the following publications from Yotaro Morishima:

Self-assembling amphiphilic polyelectrolytes and their nanostructures, Chinese Journal of Polymer Science, Vol. 18, No. 40, (2000), 323-336;

Micelle formation of random copolymers of sodium 2-(acrylamido)-2-methylpropanesulfonate and a nonionic surfactant macromonomer in water as studied by fluorescence and dynamic light scattering—Macromolecules, 2000, Vol. 33, No. 10-3694-3704;

Solution properties of micelle networks formed by nonionic moieties covalently bound to a polyelectrolyte: salt effects on rheological behavior—Langmuir, 2000 Vol. 16, No. 12, 5324-5332;

Stimuli responsive amphiphilic copolymers of sodium 2-(acrylamido)-2-methylpropanesulfonate and associative macromonomers, Polym. Preprint, Div. Polym. Chem. 1999, 40(2), 220-221.

Among these polymers, mention may be made of:
- crosslinked or non-crosslinked, neutralized or non-neutralized copolymers, comprising from 15% to 60% by weight of AMPS units and from 40% to 85% by weight of ($C_8$-$C_{16}$)alkyl(meth)acrylamide or ($C_8$-$C_{16}$)alkyl (meth)acrylate units relative to the polymer, such as those described in patent application EP-A750 899;
- terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

All these anionic associative polymers may be salified.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Among the cationic associative polymers, mention may be made of:
- (I) cationic associative polyurethanes;
- (II) the compound sold by the company Noveon under the name Aqua CC and which corresponds to the INCI name Polyacrylate-1 Crosspolymer.

Polyacrylate-1 Crosspolymer is the product of polymerization of a monomer mixture comprising:
- a di($C_1$-$C_4$ alkyl)amino($C_1$-$C_6$ alkyl) methacrylate,
- one or more $C_1$-$C_{30}$ alkyl esters of (meth)acrylic acid,
- a polyethoxylated $C_{10}$-$C_{30}$ alkyl methacrylate (20-25 mol of ethylene oxide units),
- a 30/5 polyethylene glycol/polypropylene glycol allyl ether,
- a hydroxy($C_2$-$C_6$ alkyl) methacrylate, and
- an ethylene glycol dimethacrylate.
- (III) quaternized (poly)hydroxyethylcelluloses modified with groups comprising at least one fatty chain, such as alkyl, arylalkyl or alkylaryl groups comprising at least 8 carbon atoms, or mixtures thereof. The alkyl radicals borne by the above quaternized celluloses or hydroxyethylcelluloses preferably comprise from 8 to 30 carbon atoms. The aryl radicals preferably denote phenyl, benzyl, naphthyl or anthryl groups. Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda and the product Softcat SL 100® sold by the company Aqualon.
- (IV) cationic polyvinyllactam polymers.

Such polymers are described, for example, in patent application WO-00/68282.

As cationic poly(vinyllactam) polymers according to the invention, vinylpyrrolidone/dimethylaminopropylmethacrylamide/dodecyldimethylmethacryl-amidopropylammonium tosylate terpolymers, vinylpyrrolidone/dimethylaminopropyl-methacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers are used in particular.

The amphoteric associative polymers are preferably chosen from those comprising at least one noncyclic cationic unit. Even more particularly, those prepared from or comprising 1 mol % to 20 mol %, preferably 1.5 to 15 mol % and even more particularly 1.5 to 6 mol % of fatty-chain monomer relative to the total number of moles of monomers are preferred.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

The associative polymers of nonionic type that may be used according to the invention are preferably chosen from:
- (a) copolymers of vinylpyrrolidone and of fatty-chain hydrophobic monomers, of which examples that may be mentioned include:
  - the products Antaron V216® or Ganex V216® (vinylpyrrolidone/hexadecene copolymer) sold by the company I.S.P.
  - the products Antaron V220® or Ganex V220® (vinylpyrrolidone/eicosene copolymer) sold by the company I.S.P.
- (b) copolymers of $C_1$-$C_6$ alkyl methacrylates or acrylates and of amphiphilic monomers comprising at least one fatty chain, for instance, the oxyethylenated methyl acrylate/stearyl acrylate copolymer sold by the company Goldschmidt under the name Antil 208®.
- (c) copolymers of hydrophilic methacrylates or acrylates and of hydrophobic monomers comprising at least one fatty chain, for instance the polyethylene glycol methacrylate/lauryl methacrylate copolymer.
- (d) polyurethane polyethers comprising in their chain both hydrophilic blocks usually of polyoxyethylenated nature and hydrophobic blocks, which may be aliphatic sequences alone and/or cycloaliphatic and/or aromatic sequences.
- (e) polymers with an aminoplast ether backbone containing at least one fatty chain, such as the Pure Thix® compounds sold by the company Sud-Chemie.
- (f) celluloses or derivatives thereof, modified with groups comprising at least one fatty chain, such as alkyl, arylalkyl or alkylaryl groups or mixtures thereof in which the alkyl groups are of $C_8$, and in particular:
  - nonionic alkylhydroxyethylcelluloses such as the products Natrosol Plus Grade 330 CS and Polysurf 67 ($C_{16}$ alkyl) sold by the company Aqualon;
  - nonionic nonoxynylhydroxyethylcelluloses such as the product Amercell HM-1500 sold by the company Amerchol;
  - nonionic alkylcelluloses such as the product Bermocoll EHM 100 sold by the company Berol Nobel;
- (g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisioned. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer having a hydrophilic central block) or distributed both at the ends and in the chain (for example, multiblock copolymer). These same polymers may also be graft polymers or star polymers.

The nonionic fatty-chain polyurethane polyethers may be triblock copolymers, the hydrophilic block of which is a polyoxyethylene chain comprising from 50 to 1000 oxyethylene groups. The nonionic polyurethane polyethers comprise a urethane bond between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Röhm & Haas containing a $C_{20}$ alkyl chain and a urethane bond, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Röhm & Haas may also be used.

The polyurethane polyethers that may be used according to the invention are in particular those described in the article by G. Fonnum, J. Bakke and Fk. Hansen—*Colloid Polym. Sci.*, 271, 380-389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Preferably, the thickeners are nonionic, cationic or amphoteric thickening polymers.

According to a preferred embodiment, composition (A) comprises one or more thickening polymers chosen from polysaccharides, and preferentially from cellulose-based polymers.

The pH of composition (A) is preferably between 3 and 11 and especially between 4 and 10.

The pH of these compositions (A) may be adjusted to the desired value by means of basifying agents or acidifying agents that are usually used. Among the basifying agents, examples that may be mentioned include aqueous ammonia, alkanolamines, and mineral or organic hydroxides. Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

In a preferred variant of the invention, composition (A) comprises at least one carboxylic acid, preferentially a hydroxy acid and even more preferentially lactic acid, so as to provide the pH stability and a satisfactory level of hydrolysis before mixing.

Composition (A) according to the invention may also contain additives usually used in cosmetics, such as thickeners, preserving agents, fragrances and dyes, and also most of the usual cosmetic agents for hair treatments.

These additives may be present in composition (A) according to the invention in an amount ranging from 0 to 20% by weight, relative to the total weight of composition (A).

A person skilled in the art will take care to select these optional additives and amounts thereof so that they do not harm the properties of the compositions of the present invention.

The compositions (A) according to the invention may be prepared according to the following process: two phases, each comprising at least one alkoxysilane (a) or at least one alkylalkoxysilane (b), are prepared separately. The pH of each of the phases is then adjusted before combining them. The two aqueous phases are conserved for a period of between 10 minutes and two hours, then combined in such a way that the (a)/(b) weight ratio ranges from 0.5 to 10.

In other variants of the invention, composition (A) according to the invention may be composed of several superimposed or emulsified liquid phases, or may contain suspended solid phases.

Texturing agents such as thickeners, and/or additives that are usual in cosmetics, preserving agents, fragrances and dyes, and also most of the usual cosmetic agents for hair treatments, such as silicones and cationic polymers, may be added either to at least one of the aqueous phases before mixing thereof, or after mixing thereof. In the case where it (they) is (are) added to one of the aqueous phases before mixing, this addition will preferably be to the phase that will represent the largest part of the final composition.

The compositions (A) according to the invention may be in the form of a lotion, gel, cream, paste, serum or foam.

In a particular embodiment, composition (A) comprises 0.5% to 50% by weight, relative to the total weight of the composition, of compound (a), compounds (b) and (c), and (d) one or more thickeners, said compounds being as defined above.

Composition (A) may be used on wet or dry hair, in rinse-off or leave-on mode.

A subject of the invention is also the use of composition (A) as defined previously for shaping and/or conditioning keratin fibres, especially human keratin fibres, and better still the hair.

The present invention also relates to a cosmetic treatment process, more particularly for shaping and/or conditioning the hair, which consists in applying to the hair an effective amount of a composition (A) as described above and optionally in rinsing. Preferably, composition (A) is not rinsed out.

The process according to the invention may also comprise:
  a step of applying a composition (B) comprising one or more beneficial agents bearing anionic group(s), this application preceding or following the application of composition (A), and an intermediate rinsing step optionally taking place between the application of the two compositions (A) and (B).

This process makes it possible especially to obtain beauty-enhancing properties on the hair, such as modification of the feel, and/or protection against external attacking factors such as light or heat. These properties may be readily eliminated, re-obtained, or even exchanged, via washing and simple reapplication of beneficial agents bearing anionic group(s).

Furthermore, said process improves the durability of colouring effects with respect to shampooing.

For the purposes of the present invention, the term "beneficial agent" means a cosmetic treatment agent that is capable of giving keratin fibres a cosmetic property, especially of protecting them, enhancing their beauty, conditioning them, treating them and/or holding them in shape.

For the purposes of the present invention, the term "anionic group" means a group bearing an acid function in neutralized or non-neutralized form. These anionic groups are preferably chosen from the following groups: —$CO_2H$, —$CO_2^-$, —$SO_3H$, —$SO_3^-$, —$SO_3H$, —$OSO_3^-$, —$H_2PO_3$, —$HPO_3^-$, —$PO_3^{2-}$, —$H_2PO_2$, —$HPO_2^-$, —$PO_2^{2-}$, —POH or —$PO^-$.

The beneficial agent(s) that may be used in the invention are especially chosen from:
(i) anionic surfactants and amphoteric or zwitterionic surfactants,
(ii) anionic sunscreens,
(iii) anionic polymers and amphoteric polymers; and
(iv) mixtures thereof.

As beneficial agent bearing anionic group(s), use may be made of one or more anionic surfactants or one or more amphoteric or zwitterionic surfactants.

The term "anionic surfactant" means a surfactant comprising, as ionic or ionizable groups, only anionic groups. These anionic groups are preferably chosen from the following groups: —$CO_2H$, —$CO_2^-$, —$SO_3H$, —$SO_3^-$, —$OSO_3H$, —$OSO_3^-$, —$H_2PO_3$, —$HPO_3^-$, —$PO_3^{2-}$, —$H_2PO_2$, —$HPO_2^-$, —$PO_2^{2-}$, —POH or —$PO^-$.

Mention may be made, as examples of anionic surfactants that may be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and preferably from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in the form of salts, they may be chosen from alkali metal salts such as the sodium or potassium salt and preferably the sodium salt, the ammonium salts, the amine salts and in particular the amino alcohol salts or the alkaline-earth metal salts such as the magnesium salt.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

In one particular case, the anionic surfactants may be contained in crystals or emulsions of fatty substances. These crystals or emulsions especially comprise mixtures of fatty substances in an amount of from 1% to 15% by weight and long-chain surfactants containing more than 14 carbon atoms in an amount of from 1% to 10%.

In a first variant, the anionic surfactants may be chosen from ($C_6$-$C_{24}$)alkyl sulfates, ($C_6$-$C_{24}$)alkyl ether sulfates comprising from 2 to 50 ethylene oxide units, especially in the form of alkali metal, ammonium, amino alcohol and alkaline-earth metal salts, or a mixture of these compounds.

Even better still, ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds, are preferred in this variant. Better still, ($C_{12}$-$C_{20}$)alkyl sulfates in the form of alkali metal, ammonium, amino alcohol and alkaline-earth metal salts are preferred, in particular sodium stearyl sulfate.

In a second variant, the anionic surfactants may be chosen from surfactants comprising anionic groups chosen from —C(O)OH, —C(O)O$^-$, —$SO_3H$ and —$S(O)_2O^-$, such as alkylsulfonates, alkylamide sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates, N-acyltaurates, acyl lactylates, N-acylglycinates or alkyl ether carboxylates, the alkyl and acyl groups of all these compounds comprising from 6 to 40 carbon atoms and preferably from 6 to 24 carbon atoms.

Most particularly, use may be made of ($C_{6-40}$ acyl)glutamates, better still ($C_{6-24}$ acyl)glutamates, for instance the disodium cocoyl glutamate provided under the trade name Plantapon ACG LC by the company BASF, or ($C_{6-40}$ acyl) isethionates and better still ($C_{6-24}$ acyl)isethionates, for instance the sodium lauroyl methyl isethionate sold by the company Innospec under the trade name Iselux LQ-CLR-SB.

The amphoteric or zwitterionic surfactants that can be used in the present invention may especially be derivatives of optionally quaternized secondary or tertiary aliphatic amines containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of ($C_8$-$C_{20}$)alkylbetaines, sulfobetaines, ($C_8$-$C_{20}$)alkylamido($C_1$-$C_6$)alkylbetaines such as cocoamidopropylbetaine, and ($C_8$-$C_{20}$) alkylamido($C_1$-$C_6$)alkylsulfobetaines.

Mention may also be made, among the derivatives of optionally quaternized secondary or tertiary aliphatic amines capable of being employed, of the products with respective structures (IV) and (V) below:

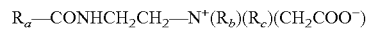

$R_a$—$CONHCH_2CH_2$—$N^+(R_b)(R_c)(CH_2COO^-)$ (IV)

in which:

R$_a$ represents a C$_{10}$-C$_{30}$ alkyl or alkenyl group derived from an acid R$_a$—COOH preferably present in hydrolysed coconut oil, or a heptyl, nonyl or undecyl group, R$_b$ represents a β-hydroxyethyl group, and R$_c$ represents a carboxymethyl group;

$$R_a\text{—CONHCH}_2\text{CH}_2\text{—N(B)(B)} \quad (V)$$

in which:

B represents —CH$_2$CH$_2$OX',

X' represents the —CH$_2$—COOH, —CH$_2$—COOZ', —CH$_2$CH$_2$—COOH or —CH$_2$CH$_2$—COOZ' group or a hydrogen atom, B' represents —(CH$_2$)$_z$—Y', with z=1 or 2, Y' represents —COOH, —COOZ', or the group —CH$_2$—CHOH—SO$_3$H or —CH$_2$—CHOH—SO$_3$Z', Z' represents an ion resulting from an alkali metal or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane.

R$_a'$ represents a C$_{10}$-C$_{30}$ alkyl or alkenyl group of an acid R$_a$—COOH preferably present in coconut oil or in hydrolysed linseed oil, an alkyl group, in particular of C$_{17}$ and its iso form, or an unsaturated C$_{17}$ group.

These compounds are also classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (Vbis):

$$R_a\text{''—NH—CH(Y'')—(CH}_2)_n\text{—C(O)—NH—} \\ \text{(CH}_2)_{n'}\text{—N(R}_d)(R_e) \quad (Vbis)$$

in which formula:

Y" represents the group —C(O)OH, —C(O)OZ", —CH$_2$—CH(OH)—SO$_3$H or the group —CH$_2$—CH(OH)—SO$_3$—Z";

R$_d$ and R$_e$, independently of each other, represent a C$_1$-C$_4$ alkyl or hydroxyalkyl group;

Z" represents a cationic counterion derived from an alkali metal or alkaline-earth metal, such as sodium, an ammonium ion or an ion derived from an organic amine;

R$_a$" represents a C$_{10}$-C$_{30}$ alkyl or alkenyl group of an acid R$_a$"—C(O)OH preferably present in coconut oil or in hydrolysed linseed oil;

n and n' denote, independently of each other, an integer ranging from 1 to 3.

Mention may be made, among the compounds of formula (Vbis), of the compound classified in the CTFA dictionary under the name sodium diethylaminopropyl cocoaspartamide and sold by Chimex under the name Chimexane HB.

Preferably, the amphoteric or zwitterionic surfactants are chosen from (C$_8$-C$_{20}$)alkylbetaines, (C$_8$-C$_{20}$)alkylamido(C$_1$-C$_6$)alkylbetaines and (C$_8$-C$_{20}$)alkyl amphodiacetates, and mixtures thereof.

An anionic surfactant will preferably be used. Better still, use will be made of an anionic surfactant such as those comprising a sulfate or sulfonic group, and in particular sodium lauryl ether sulfate, sodium lauryl sulfate, ammonium lauryl sulfate and sodium stearyl sulfate.

The anionic sunscreen(s) that may be used as beneficial agent(s) bearing anionic group(s) are chosen especially from organic UVA- and/or UVB-screening agents as described below.

Organic UVA-Screening Agents

A first example is benzene-1,4-bis(3-methylidene-10-camphorsulfonic acid) (INCI name: Terephthalylidene Dicamphor Sulfonic Acid) and the various salts thereof, described in particular in patent applications FR-A-2528420 and FR-A-2639347.

These screening agents correspond to general formula (XV) below:

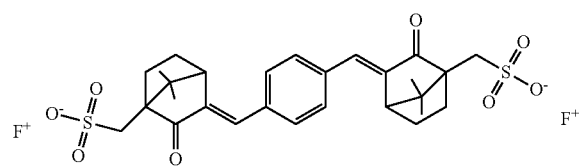

(XV)

in which F denotes a hydrogen atom, an alkali metal or a radical NH(R1)$_3^+$ in which the radicals R1, which may be identical or different, denote a hydrogen atom, a C$_1$ to C$_4$ alkyl or hydroxyalkyl radical or else a group Mn+/n, Mn+ denoting a polyvalent metal cation in which n is equal to 2 or 3 or 4, Mn+ preferably denoting a metal cation chosen from Ca$^{2+}$, Zn$^{2+}$, Mg$^{2+}$, Ba$^{2+}$, Al$^{3+}$ and Zr$^{4+}$. It is clearly understood that the compounds of formula (XV) above can give rise to the "cis-trans" isomer around one or more double bonds and that all the isomers fall within the context of the present invention.

Among the organic UVA-screening agents that can be used according to the present invention, mention may also be made of compounds comprising at least two benzazolyl groups bearing sulfonic groups, such as those described in patent application EP-A-0 669 323. They are described and prepared according to the syntheses indicated in U.S. Pat. No. 2,463,264 and also in patent application EP-A-0 669 323.

The compounds comprising at least two benzazolyl groups correspond to the general formula (XVI) below:

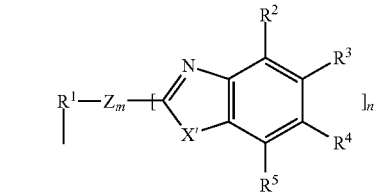

(XVI)

in which:

Z represents an organic residue of valency (1+n) comprising one or more double bonds placed such that it completes the system of double bonds of at least two benzazolyl groups as defined inside the square brackets so as to form a totally conjugated assembly;

X' denotes S, O or NR$^6$;

R$^1$ denotes hydrogen, C$_1$-C$_{18}$ alkyl, C$_1$-C$_4$ alkoxy, C$_5$-C$_{15}$ aryl, C$_2$-C$_{18}$ acyloxy, SO$_3$Y or COOY;

the radicals R$^2$, R$^3$, R$^4$ and R$^5$, which may be identical or different, denote a nitro group or a radical R$^1$;

R$^6$ denotes hydrogen, a C$_1$-C$_4$ alkyl or a C$_1$-C$_4$ hydroxyalkyl;

Y denotes hydrogen, Li, Na, K, NH$_4$, ½Ca, ½Mg, ⅓Al or a cation resulting from the neutralization of a free acid group with an organic nitrogenous base;

m is 0 or 1;

n is a number from 2 to 6;

l is a number from 1 to 4;

with the proviso that l+n does not exceed the value 6.

Among these compounds, preference is given to those for which the group Z is chosen from the group made up of:

(a1) an olefin linear aliphatic C$_2$-C$_6$ hydrocarbon-based radical which may be interrupted with a C$_5$-C$_{12}$ aryl group or a C$_4$-C$_{10}$ heteroaryl, in particular chosen from the following groups:

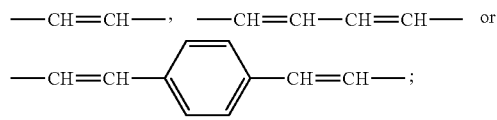

(b1) a C$_5$-C$_{15}$ aryl group which may be interrupted with an olefin linear aliphatic C$_2$-C$_6$ hydrocarbon-based radical, in particular chosen from the following groups:

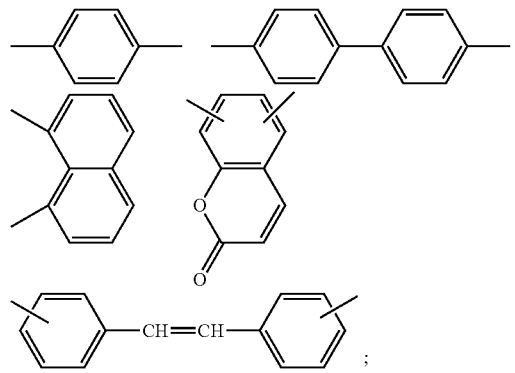

(c1) a C$_3$-C$_{10}$ heteroaryl residue, in particular chosen from the following groups:

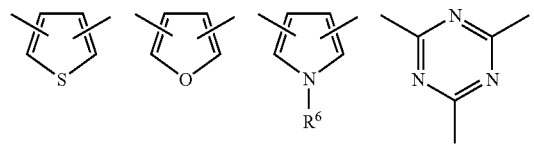

in which R$^6$ has the same meaning as that indicated above; said radicals Z as defined in paragraphs (a1), (b1) and (c1) possibly being substituted with C$_1$ to C$_6$ alkyl, C$_1$ to C$_6$ alkoxy, phenoxy, hydroxyl, methylenedioxy or amino radicals optionally substituted with one or two C$_1$-C$_5$ alkyl radicals.

Preferably, the compounds of formula (XVI) comprise, per molecule, 1, 3 or 4 groups SO$_3$Y.

As examples of compounds of formula (XVI) that may be used, mention may be made of the compounds of formulae (a') to (j') having the following structure, and also the salts thereof:

(a')
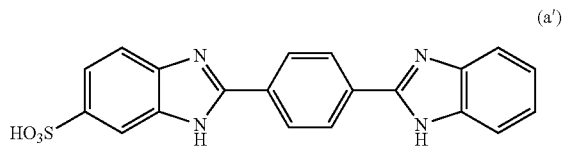

(b')
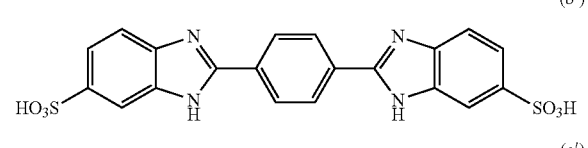

(c')
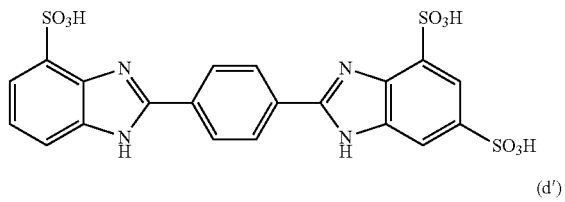

(d')
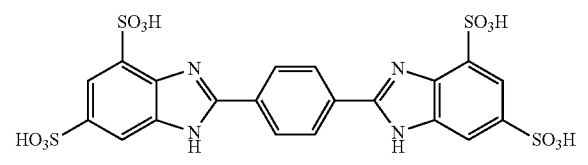 [SMILES: O=S(=O)(O)c1cc(S(=O)(=O)O)c2nc(-c3ccc(-c4nc5c(S(=O)(=O)O)cc(S(=O)(=O)O)cc5[nH]4)cc3)[nH]c2c1]

(e')
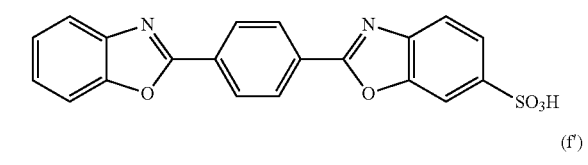

(f')
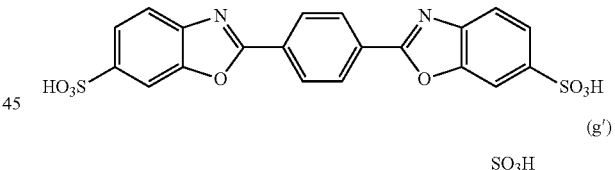

(g')
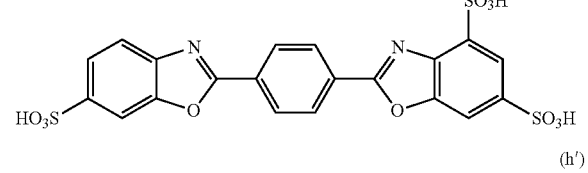

(h')
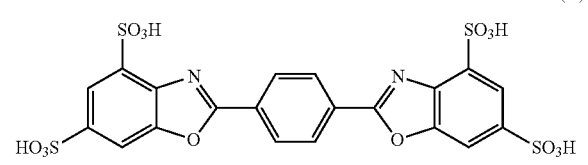

(i')
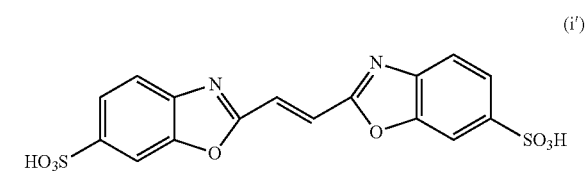

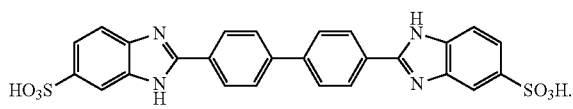

(j')

Among all these compounds, preference will most particularly be given to 1,4-bis-benzimidazolyl-phenylene-3,3', 5,5'-tetrasulfonic acid (INCI name: Disodium Phenyl Dibenzimidazole Tetrasulfonate) (compound (d')) or one of the salts thereof, having the following structure, sold under the name Neoheliopan AP® by the company Symrise:

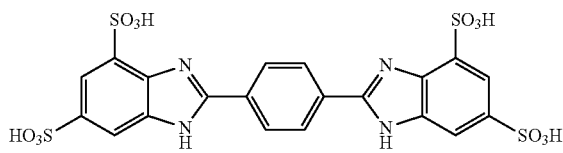

Among the organic UVA-screening agents that may be used according to the present invention, mention may also be made of benzophenone compounds comprising at least one sulfonic acid function, for instance the following compounds:

Benzophenone-4, sold by the company BASF under the name Uvinul MS40®:

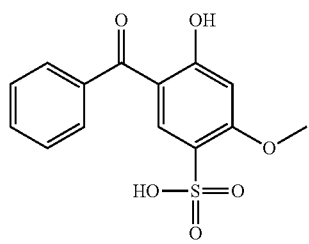 [SMILES: COc1cc(O)c(C(=O)c2ccccc2)cc1S(=O)(=O)O]

Benzophenone-5 having the structure

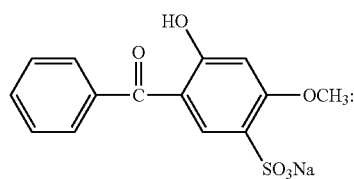

Benzophenone-9, sold by the company BASF under the name Uvinul DS49®:

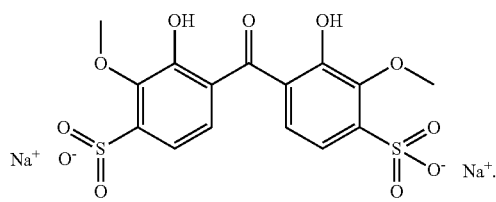

Among the organic UVA-screening agents, use will more particularly be made of benzene-1,4-bis(3-methylidene-10-camphorsulfonic acid) and the various salts thereof (INCI name: Terephthalylidene Dicamphor Sulfonic Acid) produced by the company Chimex under the trade name Mexoryl SX®.

Organic UVB-Screening Agents

The organic UVB-screening agents are especially chosen from:
hydrophilic cinnamic derivatives such as ferulic acid or 3-methoxy-4-hydroxycinnamic acid,
hydrophilic benzylidenecamphor compounds,
hydrophilic phenylbenzimidazole compounds,
hydrophilic p-aminobenzoic (PABA) compounds,
hydrophilic salicylic compounds, and
mixtures thereof.

As examples of hydrophilic organic UVB-screening agents, mention may be made of those denoted hereinbelow under their INCI name:
para-aminobenzoic compounds:
PABA,
PEG-25 PABA, sold under the name Uvinul P 25® by BASF;
salicylic compounds:
Dipropylene glycol salicylate, sold under the name Dipsal® by Scher,
TEA salicylate, sold under the name Neo Heliopan TS® by Symrise;
benzylidenecamphor compounds:
Benzylidenecamphorsulfonic acid, manufactured under the name Mexoryl SL® by Chimex,
Camphor benzalkonium methosulfate, manufactured under the name Mexoryl SO® by Chimex;
phenylbenzimidazole compounds:
Phenylbenzimidazolesulfonic acid, sold in particular under the trade name Eusolex 232® by Merck.

Use will more particularly be made of the screening agent phenylbenzimidazolesulfonic acid, sold especially under the trade name Eusolex 232® by Merck.

Preferably, the anionic sunscreens that may be used in the present invention are chosen from sulfonic screening agents, preferably from benzene-1,4-bis(3-methylidene-10-camphorsulfonic acid) and the various salts thereof; sulfonic benzophenone derivatives such as benzophenone-4; sulfonicbenzylidenecamphor derivatives, such as benzylidenecamphorsulfonic acid; phenyl benzimidazole derivatives such as phenylbenzimidazolesulfonic acid and salts thereof, disodium phenyl dibenzimidazole tetrasulfonate; and mixtures thereof.

The composition according to the invention may comprise one or more polymers bearing anionic group(s) as beneficial agent(s) bearing anionic group(s). These polymers bearing anionic group(s) may be anionic or amphoteric polymers.

The anionic polymers generally used in the present invention are polymers comprising groups derived from carboxylic acid, sulfonic acid or phosphoric acid, and having a weight-average molecular mass of between 500 and 5 000 000.

The carboxylic groups may be provided by unsaturated mono- or dicarboxylic acid monomers, such as those corresponding to the formula:

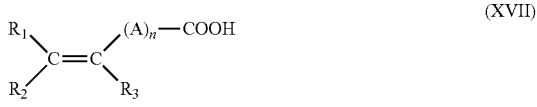

(XVII)

in which n is an integer from 0 to 10, A denotes a methylene group, optionally linked to the carbon atom of the unsaturated group or to the neighbouring methylene group when n is greater than 1, via a heteroatom such as oxygen or sulfur, $R_1$ denotes a hydrogen atom, or a phenyl or benzyl group, $R_2$ denotes a hydrogen atom or a lower alkyl or carboxyl group, $R_3$ denotes a hydrogen atom, a lower alkyl group or a —$CH_2$—COOH, phenyl or benzyl group.

The term "lower alkyl" used in the invention means a $C_1$-$C_6$, preferably $C_1$-$C_4$ alkyl group.

In formula (XVII) above, an alkyl group preferably comprises from 1 to 4 carbon atoms and in particular denotes methyl and ethyl groups.

The anionic polymers containing carboxylic groups that are preferred according to the invention are:

A) Acrylic or methacrylic acid homo- or copolymers, or salts thereof and in particular the products sold under the names Versicol® E or K by the company Allied Colloid and Ultrahold® by the company BASF, the copolymers of acrylic acid and of acrylamide sold in the form of their sodium salt under the names Reten® 421, 423 or 425 by the company Hercules, the sodium salts of polyhydroxycarboxylic acids.

B) Copolymers of acrylic or methacrylic acids with a monoethylenic monomer such as ethylene, styrene, vinyl esters and acrylic or methacrylic acid esters, optionally grafted onto a polyalkylene glycol such as polyethylene glycol and optionally crosslinked. Such polymers are described in particular in French patent 1 222 944 and German patent application 2 330 956, the copolymers of this type comprising an optionally N-alkylated and/or hydroxyalkylated acrylamide unit in their chain, as described in particular in Luxembourgian patent applications 75370 and 75371 or provided under the name Quadramer® by American Cyanamid. Mention may also be made of copolymers of acrylic acid and of $C_1$-$C_4$ alkyl methacrylate and the copolymer of methacrylic acid and of ethyl acrylate sold under the name Luvimer® MAEX by the company BASF.

C) Copolymers derived from crotonic acid, such as those whose chain comprises vinyl acetate or propionate units and optionally other monomers such as allylic or methallylic esters, vinyl ether or vinyl ester of a saturated, linear or branched carboxylic acid containing a long hydrocarbon-based chain such as those comprising at least 5 carbon atoms, it being possible for these polymers to be optionally grafted and crosslinked, or alternatively a vinyl, allyl or methallyl ester of an alpha- or beta-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by the company National Starch.

D) Polymers derived from maleic, fumaric or itaconic acids or anhydrides with vinyl esters, vinyl ethers, vinyl halides, phenylvinyl derivatives or acrylic acid and esters thereof; these polymers may be esterified. Such polymers are described in particular in U.S. Pat. Nos. 2,047,398, 2,723,248 and 2,102,113 and GB patent 839 805, and especially those sold under the names Gantrez® AN or ES by the company ISP.

Polymers also falling into this category are the copolymers of maleic, citraconic or itaconic anhydrides and of an allyl or methallyl ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the Applicant.

E) Polyacrylamides comprising carboxylate groups.

F) The polymers comprising sulfonic groups are polymers comprising vinylsulfonic, styrenesulfonic, naphthalenesulfonic or acrylamidoalkylsulfonic units.

These polymers may be chosen especially from:

polyvinylsulfonic acid salts having a molecular mass of between approximately 1000 and 100 000, and also copolymers with an unsaturated comonomer, such as acrylic or methacrylic acids and esters thereof, and also acrylamide or derivatives thereof, vinyl ethers and vinylpyrrolidone;

polystyrenesulfonic acid salts, the sodium salts having a molecular mass of about 500 000 and of about 100 000, sold, respectively, under the names Flexan® 500 and Flexan® 130 by National Starch. These compounds are described in patent FR 2198719;

polyacrylamidesulfonic acid salts, such as those mentioned in U.S. Pat. No. 4,128,631 and more particularly the polyacrylamidoethylpropanesulfonic acid sold under the name Cosmedia Polymer® HSP 1180 by Henkel.

G) Anionic silicones.

Preferably, the anionic polymers are chosen from (meth) acrylic polymers and sulfonic polymers, such as those of families A), B) and F), better still from (meth)acrylic polymers.

According to the invention, the anionic polymers are even more particularly chosen from acrylic acid copolymers such as the acrylic acid/ethyl acrylate/N-tert-butylacrylamide terpolymer sold under the name Ultrahold Strong® by the company BASF, the copolymers of methacrylic acid and of methyl methacrylate sold under the name Eudragit® L by the company Röhm Pharma, the copolymer of methacrylic acid and of ethyl acrylate sold under the name Luvimer® MAEX by the company BASF, and from copolymers derived from crotonic acid, such as the vinyl acetate/vinyl tert-butylbenzoate/crotonic acid terpolymers and the crotonic acid/vinyl acetate/vinyl neododecanoate terpolymers sold especially under the name Resyn 28-2930 by the company AkzoNobel.

Better still, the anionic polymers are chosen from the copolymers of methacrylic acid and of methyl methacrylate sold under the name Eudragit® L by the company Röhm Pharma, and the copolymer of methacrylic acid and of ethyl acrylate sold under the name Luvimer® MAEX by the company BASF.

According to the invention, use may also be made of anionic latices or pseudo latices, i.e. aqueous dispersions of insoluble polymer particles.

It is also possible to use amphoteric polymers as beneficial agents bearing anionic group(s).

The amphoteric polymers may be chosen from polymers comprising units deriving:

a) from at least one monomer chosen from acrylamides and methacrylamides substituted on the nitrogen atom with an alkyl group, b) from at least one acidic comonomer containing one or more reactive carboxylic groups, and c) from at least one basic comonomer such as esters with primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers of which the INCI name is Octylacrylamide/acrylates/butylaminoethyl methacrylate copolymer, such as the products sold under the names Amphomer®, Amphomer® LV71 or Balance® 47 by the company Akzo Nobel, are particularly used.

The amphoteric polymers may also be chosen from amphoteric polymers comprising the repetition of:

(i) one or more units derived from a (meth)acrylamide-type monomer, (ii) one or more units derived from a monomer of (meth)acrylamidoalkyltrialkylammonium type, and (iii) one or more units derived from a (meth)acrylic acid-type acid monomer.

Preferably, the units derived from a monomer of (meth)acrylamide type are units of structure (XVIII) below:

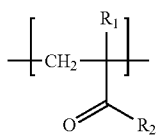

(XVIII)

in which $R_1$ denotes H or $CH_3$ and $R_2$ is chosen from an amino, dimethylamino, tert-butylamino, dodecylamino or —NH—$CH_2$OH radical.

Preferably, said amphoteric polymer comprises the repetition of only one unit of formula (XVIII).

The unit derived from a monomer of (meth)acrylamide type of formula (XVIII) in which $R_1$ denotes H and $R_2$ is an amino radical ($NH_2$) is particularly preferred. It corresponds to the acrylamide monomer itself.

Preferably, the units derived from a monomer of (meth)acrylamidoalkyltrialkylammonium type are units of structure (XIX) below:

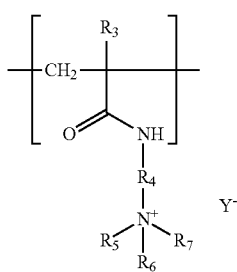

(XIX)

in which:

$R_3$ denotes H or $CH_3$, $R_4$ denotes a group $(CH_2)_k$— with k being an integer ranging from 1 to 6 and preferably from 2 to 4;

$R_5$, $R_6$ and $R_7$, which may be identical or different, denote a $C_1$-$C_4$ alkyl, $Y^-$ is an anion such as bromide, chloride, acetate, borate, citrate, tartrate, bisulfate, bisulfite, sulfate or phosphate.

Preferably, said amphoteric polymer comprises the repetition of only one unit of formula (XIX).

Among these units derived from a monomer of (meth)acrylamidoalkyltrialkylammonium type of formula (XIX), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the units derived from a monomer of (meth)acrylic acid type are units of formula (XX):

(XX)

in which $R_8$ denotes H or $CH_3$ and $R_9$ denotes a hydroxyl radical or an —NH—$C(CH_3)_2$—$CH_2$—$SO_3$H radical.

The preferred units of formula (XX) correspond to the acrylic acid, methacrylic acid and 2-acrylamino-2-methylpropanesulfonic acid monomers.

Preferably, the unit derived from a monomer of (meth)acrylic acid type of formula (XX) is that derived from acrylic acid, for which $R_8$ denotes a hydrogen atom and $R_9$ denotes a hydroxyl radical.

The acidic monomer(s) of (meth)acrylic acid type may be non-neutralized or partially or totally neutralized with an organic or mineral base.

Preferably, said amphoteric polymer comprises the repetition of only one unit of formula (XX).

According to a preferred embodiment of the invention, the amphoteric polymer or polymers of this type comprise at least 30 mol % of units derived from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth)acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:

from 30 mol % to 70 mol % and more preferably from 40 mol % to 60 mol % of units derived from a monomer of (meth)acrylamide type (i), from 10 mol % to 60 mol % and preferentially from 20 mol % to 55 mol % of units derived from a monomer of (meth)acrylamidoalkyltrialkylammonium type (ii), and from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, said amphoteric polymers are constituted solely of units derived from monomers of (meth)acrylamide type (i), of (meth)acrylamidoalkyltrialkylammonium type (ii) and of (meth)acrylic acid type (iii).

Mention may be made, as an example of particularly preferred amphoteric polymers, of acrylamide/methacrylamidopropyltrimethylammonium chloride/acrylic acid terpolymers. Such polymers are listed in the CTFA dictionary (INCI) under the name "Polyquaternium 53". Corresponding products are in particular sold under the names Merquat 2003 and Merquat 2003 PR by the company Nalco.

As another type of amphoteric polymer that may be used, mention may also be made of copolymers based on (meth) acrylic acid and on a dialkyldiallylammonium salt, such as copolymers of (meth)acrylic acid and of dimethyldiallylammonium chloride. An example that may be mentioned is Merquat 280 sold by the company Nalco.

Preferably, use is made of the copolymers whose INCI name is Octylacrylamide/acrylates/butylaminoethyl methacrylate copolymer, such as the products sold under the names Amphomer®, Amphomer® LV71 or Balance® 47 by the company AkzoNobel.

Preferably, the polymer(s) bearing anionic group(s) that may be used as beneficial agent(s) bearing anionic group(s) are one or more anionic polymers such as those described above, such as (meth)acrylic polymers, and mixtures thereof.

Preferably, the beneficial agents bearing anionic group(s) are chosen from anionic surfactants such as those comprising a sulfate or sulfonic group, sulfonic sunscreens, and anionic polymers such as (meth)acrylic polymers, and mixtures thereof.

Better still, the beneficial agent(s) bearing anionic group (s) are chosen from sodium stearyl sulfate, sodium lauryl ether sulfate, sodium lauryl sulfate, ammonium lauryl sulfate, terephthalylidenedicamphorsulfonic acid, acrylic acid/ ethyl acrylate/N-tert-butylacrylamide terpolymers and vinyl acetate/vinyl tert-butylbenzoate/crotonic acid terpolymers and crotonic acid/vinyl acetate/vinyl neododecanoate terpolymers, and the octylacrylamide/acrylates/butylaminoethyl methacrylate copolymer, and mixtures thereof.

Said anionic beneficial agent(s) used in composition (B) according to the invention may represent from 0.001% to 20% by weight, preferably from 0.01% to 15% by weight and in particular from 0.05% to 10% by weight, relative to the total weight of composition (B).

Composition (B) preferably comprises a cosmetically acceptable medium which preferably comprises water, one or more organic solvents such as those described above for composition (A), or a mixture thereof.

Preferably, the amount of water ranges from 30% to 99.95% by weight, better still from 50% by weight to 99.92% by weight, even better still from 60% to 99.92% by weight and even more preferentially from 80% to 99% by weight, relative to the total weight of composition (B).

The pH of composition (B) is preferably between 3 and 11 and especially between 4 and 10.

Composition (B) according to the invention may also contain additives usually used in cosmetics, such as thickeners, preserving agents, fragrances and dyes, and also most of the usual cosmetic agents for hair treatments.

These additives may be present in composition (B) according to the invention in an amount ranging from 0 to 20% by weight, relative to the total weight of a composition.

In one particular embodiment, composition (A) is applied either before or after composition (B). An intermediate rinsing step may optionally take place between the application of compositions (A) and (B).

In a preferred variant of the invention, composition (A) is applied before composition (B). In another variant of the invention, composition (B) is applied before composition (A).

Composition (B) may be used on wet or dry hair, in rinse-off or leave-on mode.

Composition (B) is in the form of a lotion, a gel, an emulsion, a cream or a paste.

A heating step may be envisaged after the two compositions (A) and (B) have been applied, for example using a straightening iron regulated at a temperature preferably ranging from 150° C. to 230° C., better still from 200° C. to 220° C.

According to a preferred embodiment of the invention, the process will be performed by applying composition (A), intermediate drying, applying composition (B) and then rinsing and drying the hair.

The present invention also relates to a multi-compartment device, or kit, for treating keratin fibres, comprising at least two compartments:
  a first compartment containing a composition (A) as described in the present application; and
  a second compartment including a composition (B) comprising one or more anionic beneficial agents.

In one variant, the device according to the invention comprises at least three compartments:
  a first compartment containing a composition (A1) comprising one or more alkoxysilanes bearing solubilizing function(s) (a) as described above; and
  a second compartment containing a composition (A2) comprising one or more alkylalkoxysilanes (b) as described above; and
  a third compartment containing a composition (B) comprising one or more anionic beneficial agents.

Compositions (A1), (A2) and (B) may comprise a cosmetically acceptable medium as described above.

Compositions (A1), (A2) and (B) may also comprise additives that are usually used in cosmetics, as described above.

The invention is illustrated by the examples that follow.

EXAMPLES

Example 1

Compositions according to the invention are prepared from the ingredients indicated in the table below. All the percentages are by weight and the amounts indicated are expressed as % by weight of product in its existing form, relative to the total weight of the composition.

|                                          | Formulation |     |      |     |
|------------------------------------------|-------------|-----|------|-----|
|                                          | 1           | 2   | 3    | 4   |
| Aminopropyltriethoxysilane               | 5           | 5   | 5    | 7.5 |
| Methyltriethoxysilane                    | 1.5         | 1.5 | 3    | 2.25|
| Lactic acid (90% of active material (AM))| —           | 1.9 | —    | 2.8 |
| Hydrochloric acid (33.5% of AM)          | —           | —   | 1.25 | —   |
| Water qs                                 | 100         | 100 | 100  | 100 |

|                                      | Formulation |      |     |     |      |      |     |
|--------------------------------------|-------------|------|-----|-----|------|------|-----|
|                                      | 5           | 6    | 7   | 8   | 9    | 10   | 11  |
| Aminopropyltriethoxysilane           | 10          | 10   | 10  | 10  | 10   | 10   | 10  |
| Methyltriethoxysilane                | 1.5         | 1.5  | 3   | 3   | 3    | 3    | 3   |
| Lactic acid (90% of AM)              | 2.5         | 3.75 | —   | —   | 0.87 | 1.05 | 2.5 |
| Hydrochloric acid (33.5% by weight of AM) | —      | —    | —   | 2.5 | —    | —    | —   |
| Water qs                             | 100         | 100  | 100 | 100 | 100  | 100  | 100 |

|                                | Formulation |     |     |     |     |
|--------------------------------|-------------|-----|-----|-----|-----|
|                                | 12          | 13  | 14  | 15  | 16  |
| Aminopropyltriethoxysilane     | 10          | 20  | 20  | 20  | 10  |
| Methyltriethoxysilane          | 3           | 3   | 6   | 6   | 3   |
| Lactic acid (90% of AM)        | 6           | 5   | 5   | —   | 6   |
| Hydrochloric acid (33.5% of AM)| —           | —   | —   | 5   | —   |
| Ethanol                        | —           | —   | —   | —   | 20  |
| Water qs                       | 100         | 100 | 100 | 100 | 100 |

|                                                         | Formulation |     |     |     |     |      |
|---------------------------------------------------------|-------------|-----|-----|-----|-----|------|
|                                                         | 17          | 18  | 19  | 20  | 21  | 22   |
| Aminopropyltriethoxysilane                              | 5           | 5   | 10  | 10  | 10  | 10   |
| Methyltriethoxysilane                                   | 1.5         | 1.5 | 3   | 3   | 3   | 3    |
| Lactic acid (90% of AM)                                 | 2           | 3   | 3.5 | 3.5 | 6   | 6    |
| Hydroxyethylcellulose (Natrosol 250 HHR - Ashland)      | 0.7         | 0.7 | —   | 1.5 | 1.5 | 2    |
| Polysorbate 20                                          | 0.5         | —   | 0.5 | —   | —   | 0.75 |
| Polyoxyethylenated (PEG-40) and hydrogenated castor oil | 0.5         | —   | 0.5 | —   | —   | 0.75 |
| Phenoxyethanol                                          | 0.7         | —   | 0.7 | —   | 0.7 | 0.7  |
| Methylisothiazolinone (9.5% of AM)                      | 0.1         | —   | 0.1 | —   | 0.1 | 0.1  |
| Fragrance                                               | 0.5         | —   | 0.5 | —   | —   | 0.75 |
| Water qs                                                | 100         | 100 | 100 | 100 | 100 | 100  |

|                                                                                       | Formulation |     |     |     |      |
|---------------------------------------------------------------------------------------|-------------|-----|-----|-----|------|
|                                                                                       | 23          | 24  | 25  | 26  | 27   |
| Aminopropyltriethoxysilane                                                            | 10          | 10  | 10  | 5   | 10   |
| Methyltriethoxysilane                                                                 | 3           | 3   | 3   | 1.5 | 3    |
| Lactic acid (90% of AM)                                                               | 3.5         | 3.5 | 6   | 3   | 6    |
| Hydroxyethylcellulose (Natrosol 250 HHR - Ashland)                                    | —           | —   | 2   | 2   | 2    |
| Methylethyl hydroxyethylcellulose (Structure Cel 8000M - AkzoNobel)                   | —           | 1.5 | —   | —   | —    |
| Steareth-100/PEG-136/hexamethylene diisocyanate (HDI) copolymer (Rheoluxe 811, Elementis) | 4       | —   | —   | —   | —    |
| Ethanol                                                                               | —           | —   | —   | 20  | 20   |
| Polysorbate 20                                                                        | —           | —   | 0.75| 0.5 | 0.75 |
| Polyoxyethylenated (PEG-40) and hydrogenated castor oil                               | —           | —   | 0.75| 0.5 | 0.75 |
| Phenoxyethanol                                                                        | —           | —   | 0.7 | 0.7 | 0.7  |
| Methylisothiazolinone (9.5% of AM)                                                    | —           | —   | 0.1 | 0.1 | 0.1  |

-continued

|  | 23 | 24 | 25 | 26 | 27 |
|---|---|---|---|---|---|
| Fragrance | — | — | 0.75 | 0.5 | 0.75 |
| Water qs | 100 | 100 | 100 | 100 | 100 |

| | Formulation |||||||
|---|---|---|---|---|---|---|---|
| | 28 | 29 | 30 | 31 | 32 | 33 | 34 |
| Aminopropyltriethoxysilane | 5 | 5 | 5 | 5 | 5 | 10 | 10 |
| Methyltriethoxysilane | 1.5 | 1.5 | 1.5 | 1.5 | 1.5 | 3 | 3 |
| Lactic acid (90% of A.M.) | 2 | 1.75 | 1.75 | 1.75 | 1.75 | 1 | 3.5 |
| Hydroxyethylcellulose (Natrosol 250 HHR - Ashland) | 0.7 | 1.5 | 1.5 | 1.5 | 1.5 | — | — |
| Polyquaternium-4 (Cellquat LOR AkzoNobel) | — | — | — | — | — | 1 | — |
| Polyquaternium-6 (Merquat-100 Lubrizol) | 3 | — | — | — | — | — | — |
| Vinylpyrrolidone/ dimethylamino-ethyl methacrylate copolymer (20% of AM) (Copolymer 845-0 Ashland) | — | — | 12 | 17 | — | — | — |
| Vinylamine/vinylformamide copolymer (13% of AM) (Luviquat 9030 BASF) | — | 6.25 | — | — | 9 | — | — |
| Polyquaternium-86 (Luvigel Advanced BASF) | — | — | — | — | — | — | 3 |
| Polysorbate 20 | 0.5 | — | — | — | — | — | — |
| Polyoxyethylenated (PEG-40) and hydrogenated castor oil | 0.5 | — | — | — | — | — | — |
| Phenoxyethanol | 0.7 | — | — | — | — | — | — |
| Methylisothiazolinone (9.5% of AM) | 0.1 | — | — | — | — | — | — |
| Fragrance | 0.5 | — | — | — | — | — | — |
| Water qs | 100 | 100 | 100 | 100 | 100 | 100 | 100 |

| | Formulation |||
|---|---|---|---|
| | 35 | 36 | 37 |
| Aminopropyltriethoxysilane | 10 | 5 | 10 |
| Methyltriethoxysilane | 3 | 1.5 | 3 |
| Lactic acid (containing 90% by weight of AM) | 0.87 | 1.75 | 4 |
| Hydroxyethylcellulose (Natrosol 250 HHR - Ashland) | — | 1.5 | — |
| Vinylpyrrolidone/vinyl acrylate copolymer (50% of AM) (Luviskol VA 64 W BASF) | 2 | 16 | — |
| Isododecane | — | — | 20 |
| Water qs | 100 | 100 | 100 |

| | Comparative example ||||
|---|---|---|---|---|
| | 1 | 2 | 3 | 4 |
| Aminopropyltriethoxysilane | — | — | 10 | 20 |
| Methyltriethoxysilane | 1.5 | 6 | — | — |
| Lactic acid (90% of AM) | qs pH 3 | qs pH 3 | 6 | 6 |
| Water qs | 100 | 100 | 100 | 100 |

The general preparation mode for the above compositions is as follows: at room temperature, the methyltriethoxysilane was added to half the water used for the composition, followed by part of the pH agent (lactic acid or hydrochloric acid) to reach pH 3.

Separately, the aminopropyltriethoxysilane was mixed with the remaining water useful for the composition and the rest of the pH agent.

After having obtained a homogeneous first mixture, the two solutions were combined and the other ingredients were then added.

Locks of natural wet hair were treated with formulations 1-37.

In particular, formulation 20 was applied at a rate of 150 mg per gram of hair over the entire length of the lock. After drying, the lock of hair was placed horizontally, blocked by a jaw at the hair attachment and the angle it made with the horizontal was observed, and also the maintenance of this angle after series of mechanical stresses (crushing of the lock in flat tongs, which are drawn over the entire length). The level of fixing obtained was equivalent to that of a fixing gel based on common polymers such as crosslinked acrylates/$C_{10-30}$ alkyl acrylate polymer, vinylpyrrolidone/vinyl acetate copolymer and vinylpyrrolidone/dimethylamino-ethyl methacrylate copolymer.

In addition, the lock thus treated with formulation 20 is more resistant to the mechanical stress: it withstands eight passages of the flat tongs. However, a lock treated with the above fixing gel, which makes it possible to obtain the same level of fixing, breaks after two passages.

In addition, the locks treated with formulation 20 retained a soft feel, and an absence of residue formation was observed.

Other locks of wet hair were then treated with formulation 17 in the same manner as above and compared with a reference formulation used for giving hairstyles moisture resistance, based on behenyltrimethylammonium chloride, stearyl alcohol, amodimethicone, trideceth-6 and cetyltrimethylammonium chloride, dimethicone, laureth-4 and laureth-23 and PPG-5-ceteth-20.

The moisture resistance of the locks was then evaluated after drying with a hairdryer. Eight locks treated with formulation 17 were placed in a chamber at controlled humidity (80%) for 24 hours at 25° C. The eight locks thus treated remain non-tacky and regain very little volume in comparison with eight other locks treated with the reference formulation (56% vs 71%, respectively, expressed as effective area by analysis of photographs of the locks: area delimited by the contour of the lock).

The compositions of comparative examples 1 and 2 are unstable and were not able to be evaluated.

The compositions of comparative examples 3 and 4 are tacky and do not deliver sufficient fixing performance.

Furthermore, bleached locks, treated with compositions 17 or 20 and then dried, were subsequently washed with a commercial shampoo based on sodium lauryl ether sulfate and cocoyl betaine. They were then rinsed and it was observed that the disentangling was markedly easier than for untreated locks or locks treated with usual styling compositions.

Example 2

The pretreatment compositions (A) and the post-treatment compositions (B) were prepared, using the ingredients indicated in the tables below. All the percentages are by weight and the amounts indicated are expressed as % by weight of product in its existing form, relative to the total weight of each composition.

| | Pretreatment composition (A) | | | | |
|---|---|---|---|---|---|
| | A1 | A2 | A3 | A4 | A5 |
| Aminopropyl-triethoxysilane | 5 | 5 | 10 | 10 | 10 |
| Methyltriethoxysilane | 1.5 | 1.5 | 1.5 | 1.5 | 1.5 |
| Lactic acid | 1.75* | 3** | 2.5* | 6** | 3.75 |
| Water qs | 100 | 100 | 100 | 100 | 100 |

*and qs pH 9;
**and qs pH 5

| | Post-treatment composition (B) | | | |
|---|---|---|---|---|
| | B2 | B3 | B4 | B5 |
| Sodium stearyl sulfate | 1 | 2 | 3 | — |
| Cetearyl alcohol | 3 | 4 | 7 | — |
| Mexoryl SX | — | — | — | 0.25 |
| Water qs | 100 | 100 | 100 | 100 |

Compositions A1 to A5 were first prepared in the following manner: an aqueous solution comprising half the final amount of water and the lactic acid was prepared in an amount such that the pH is equal to 3, and this solution was then mixed with the methyltriethoxysilane. The mixture was stirred for 30 minutes at room temperature.

In parallel, the aminopropyltriethoxysilane was diluted in the other half of the final amount of water, and the remaining amount of lactic acid was added thereto, followed, after 30 minutes, by the solution obtained with the methyltriethoxysilane. If necessary, the mixture was made up with water to obtain the desired amount of formulation.

Next, each composition was applied to locks of natural, dyed or sensitized wet or dry hair, in an amount of 150 mg per gram of hair (in leave-in mode) or 400 mg per gram of hair (in rinse-out mode). After a leave-on time of 5 minutes, the hair was dried, or was rinsed with water and then dried. The drying is natural, or else is facilitated by applying the heat of a hairdryer, optionally flat tongs.

After this pretreatment, the locks were wetted and compositions B2 to B5 were applied in an amount of 400 mg of composition per gram of hair. After a leave-on time of 5 minutes, the hair is rinsed with water and then dried. The hair is dried naturally, or else heat is applied using a hairdryer, optionally flat tongs.

With compositions B2 to B4, the locks obtained are very easy to disentangle, when the hair is wet or dry. In addition, they remain supple during the subsequent application of a shampoo.

Chestnut-brown or artificially dyed locks, pretreated with one of the formulations A1 to A5 and then treated with composition B5, show much better resistance to UV exposure than the untreated chestnut-brown or dyed locks.

Persistence of the cosmetic properties obtained, after several shampoo washes, is also obtained.

Example 3

Formulation 38 according to the invention and comparative formulation 39 were prepared from the ingredients indicated in the table below. All the percentages are by weight and the amounts indicated are expressed as % by weight of active material, relative to the total weight of the formulation.

| | 38 (Invention) | 39 (Comparative) |
|---|---|---|
| Octyltriethoxysilane (Dynasilan OCTEO - EVONIK) | — | 5 |
| Methyltriethoxy silane (MTES) | 5 | — |
| Aminopropyltriethoxysilane (XIAMETER OFS-6011 SILANE - DOW CORNING) | 5 | 5 |
| Coco glucoside (PLANTACARE 818 UP - COGNIS) | 1 | 1 |
| Hydroxyethylcellulose (Natrosol 250 HHR PC - ASHLAND) | 0.6 | 0.6 |
| Lactic acid | 2 | 2 |
| Eau | Qs 100 | Qs 100 |

The stability of both formulations was evaluated. After their preparation, they were stored for 7 days in an oven at 66° C.

After 7 days, a phase separation was observed for formulation 39 whereas formulation 38 remains homogeneous.

Therefore, formulation 38 according to the invention has an improved stability when compared to that of comparative formulation 39.

The invention claimed is:

1. A process for shaping and/or caring for hair, the process comprising applying a composition (A) comprising:
   (a) at least one alkoxysilane bearing at least one solubilizing function of formula (I) below, and/or oligomers thereof:

$$R_1Si(OR_2)_z(R_3)_x(OH)_y \tag{I}$$

wherein:
R₁ is a linear or branched, saturated or unsaturated, cyclic or acyclic $C_1$-$C_6$ hydrocarbon-based chain substituted with one or more groups chosen from the following groups:
amine $NH_2$ or NHR, R being:
i) a $C_1$-$C_{20}$ alkyl group optionally substituted with a group comprising a silicon atom,
ii) a $C_3$-$C_{40}$ cycloalkyl group, or
iii) a $C_6$-$C_{30}$ aromatic group,
hydroxyl,
thiol, or
aryl or aryloxy which is or unsubstituted, or optionally substituted with an amino group or with a $C_1$-$C_4$ aminoalkyl group,
R₁ optionally being interrupted with a heteroatom chosen from O, S or NH, or a carbonyl group (CO),
R₂ and R₃, which may be identical or different, each represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with the proviso that z+x+y=3,
(b) at least one alkylalkoxysilane of formula (III) below, and/or oligomers thereof:

wherein:
R4 and R5 each represent, independently of each other, a $C_{1-6}$ alkyl group,
n ranges from 1 to 3,
m ranges from 1 to 3,
with the proviso that m+n=4, and
(c) water in an amount of greater than 30% by weight relative to the total weight of the composition,
wherein compounds (a) and (b) are present in an (a)/(b) weight ratio ranging from 1 to 10;
wherein the oligomers of the at least one alkoxysilane are polymerization products of the at least one alkoxysilane and the oligomers of the at least one alkylalkoxysilane are polymerization products of the at least one alkylalkoxysilane, and wherein the oligomers of both the at least one alkoxysilane and the at least one alkylalkoxysilane comprise from 2 to 10 silicon atoms.

2. The process according to claim 1, wherein R₁ is a linear or branched, saturated or unsaturated C1-C6 hydrocarbon-based chain, substituted with an amine group $NH_2$ or NHR, R being:
i) a $C_1$-$C_{20}$ alkyl group optionally substituted with a group comprising a silicon atom,
ii) a $C_3$-$C_{40}$ cycloalkyl, or
iii) a $C_6$-$C_{30}$ aromatic group.

3. The process according to claim 1, wherein R2 represents an alkyl group comprising from 1 to 4 carbon atoms.

4. The process according to claim 1, wherein the alkoxysilane bearing at least one solubilizing function (a) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and bis[3-(triethoxysilyl)propyl]amine, oligomers thereof, or mixtures thereof.

5. The process according to claim 1, wherein the alkoxysilane bearing at least one solubilizing function (a) is chosen from those of formula (II) and/or oligomers thereof:

wherein the groups R', which may be identical or different, are each chosen from linear or branched $C_1$-$C_6$ alkyl groups and n" is an integer ranging from 1 to 6.

6. The process according to claim 1, wherein the alkoxysilane bearing at least one solubilizing function (a) is present in an amount ranging from 0.5% to 50% by weight, relative to the total weight of the composition.

7. The process according to claim 1, wherein in formula (III), R₅ represents a methyl, ethyl, or n-propyl group; n=3; and m=1.

8. The process according to claim 1, wherein the alkylalkoxysilane (b) is chosen from methyltriethoxysilane (MTES), methyltripropyloxysilane, or oligomers thereof.

9. The process according to claim 1, wherein the alkylalkoxysilane (b) is present in an amount ranging from 0.1% to 50% by weight, relative to the total weight of the composition.

10. The process according to claim 1, wherein water is present in an amount ranging from 30% to 99% by weight, relative to the total weight of the composition.

11. A composition comprising:
(a) 0.5% to 50% by weight, relative to the total weight of the composition, of at least one alkoxysilane bearing at least one solubilizing function of formula (I) below, and/or oligomers thereof:

wherein:
R₁ is a linear or branched, saturated or unsaturated, cyclic or acyclic $C_1$-$C_6$ hydrocarbon-based chain substituted with one or more groups chosen from the following groups:
amine $NH_2$ or NHR, R being:
i) a $C_1$-$C_{20}$ alkyl group optionally substituted with a group comprising a silicon atom,
ii) a $C_3$-$C_{40}$ cycloalkyl group, or
iii) a $C_6$-$C_{30}$ aromatic group,
hydroxyl,
thiol, or
aryl or aryloxy which is substituted or unsubstituted, or optionally substituted with an amino group or with a $C_1$-$C_4$ aminoalkyl group,
R₁ optionally being interrupted with a heteroatom chosen from O, S or NH, or a carbonyl group (CO),
R₂ and R₃, which may be identical or different, each represent a linear or branched alkyl group comprising from 1 to 6 carbon atoms,
y denotes an integer ranging from 0 to 3,
z denotes an integer ranging from 0 to 3, and
x denotes an integer ranging from 0 to 2,
with the proviso that z+x+y=3,
(b) at least one alkylalkoxysilane of formula (III) below, and/or oligomers thereof:

wherein:
R₄ and R₅ each represent, independently of each other, a $C_{1-6}$ alkyl group,
n ranges from 1 to 3,
m ranges from 1 to 3,
with the proviso that m+n=4,
(c) water in an amount of greater than 30% by weight relative to the total weight of the composition, and
(d) at least one thickener,
wherein compounds (a) and (b) are present in an (a)/(b) weight ratio ranging from 1 to 10;

wherein the oligomers of the at least one alkoxysilane are polymerization products of the at least one alkoxysilane and the oligomers of the at least one alkylalkoxysilane are polymerization products of the at least one alkylalkoxysilane, and wherein the oligomers of both the at least one alkoxysilane and the at least one alkylalkoxysilane comprise from 2 to 10 silicon atoms.

12. A process for shaping and/or conditioning the hair, the process comprising applying a composition comprising:
(a) at least one alkoxysilane bearing at least one solubilizing function of formula (I) below, and/or oligomers thereof:

$$R_1Si(OR_2)_z(R_3)_x(OH)_y \quad (I)$$

wherein:
  $R_1$ is a linear or branched, saturated or unsaturated, cyclic or acyclic $C_1$-$C_6$ hydrocarbon-based chain substituted with one or more groups chosen from the following groups:
    amine $NH_2$ or NHR, R being:
      i) a $C_1$-$C_{20}$ alkyl group optionally substituted with a group comprising a silicon atom,
      ii) a $C_3$-$C_{40}$ cycloalkyl group, or
      iii) a $C_6$-$C_{30}$ aromatic group,
    hydroxyl,
    thiol, or
    aryl or aryloxy which is substituted or unsubstituted, or optionally substituted with an amino group or with a $C_1$-$C_4$ aminoalkyl group,
  $R_1$ optionally being interrupted with a heteroatom chosen from O, S or NH, or a carbonyl group (CO),
  $R_2$ and $R_3$, which may be identical or different, each represent a linear or branched alkyl group comprising from 1 to 6 carbon atoms,
  y denotes an integer ranging from 0 to 3,
  z denotes an integer ranging from 0 to 3, and
  x denotes an integer ranging from 0 to 2,
  with the proviso that z+x+y=3,
(b) at least one alkylalkoxysilane of formula (III) below, and/or oligomers thereof:

$$(R_4)_mSi(OR_5)_n \quad (III)$$

wherein:
  $R_4$ and $R_5$ each represent, independently of each other, a $C_{1-6}$ alkyl group,
  n ranges from 1 to 3,
  m ranges from 1 to 3,
  with the proviso that m+n=4,
(c) water in an amount of greater than 30% by weight relative to the total weight of the composition, and
(d) at least one thickener,
wherein compounds (a) and (b) are present in an (a)/(b) weight ratio ranging from 1 to 10;
wherein the oligomers of the at least one alkoxysilane are polymerization products of the at least one alkoxysilane and the oligomers of the at least one alkylalkoxysilane are polymerization products of the at least one alkylalkoxysilane, and wherein the oligomers of both the at least one alkoxysilane and the at least one alkylalkoxysilane comprise from 2 to 10 silicon atoms.

* * * * *